US012575591B2

(12) United States Patent
Yadav

(10) Patent No.: US 12,575,591 B2
(45) Date of Patent: Mar. 17, 2026

(54) COMPOSITIONS USEFUL FOR DIETARY SUPPLEMENTS

(71) Applicant: Wake Forest University Health Sciences, Winston-Salem, NC (US)

(72) Inventor: Hariom Yadav, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 616 days.

(21) Appl. No.: 17/072,630

(22) Filed: Oct. 16, 2020

(65) Prior Publication Data

US 2021/0112841 A1     Apr. 22, 2021

Related U.S. Application Data

(60) Provisional application No. 62/916,622, filed on Oct. 17, 2019.

(51) Int. Cl.
*A23L 29/231* (2016.01)
*A23C 9/123* (2006.01)
*A23L 33/00* (2016.01)
*A23L 33/135* (2016.01)
*A61K 9/20* (2006.01)
*A61K 9/48* (2006.01)

(52) U.S. Cl.
CPC .......... *A23L 29/231* (2016.08); *A23C 9/1234* (2013.01); *A23L 33/135* (2016.08); *A23L 33/30* (2016.08); *A61K 9/20* (2013.01); *A61K 9/48* (2013.01); *A23V 2400/11* (2023.08)

(58) Field of Classification Search
CPC ... A23L 33/125; A23L 33/135; A23C 9/1234; A23Y 2220/00
See application file for complete search history.

(56) References Cited

U.S. PATENT DOCUMENTS

| | | | |
|---|---|---|---|
| 7,097,831 B1 * | 8/2006 | Bengs ................... | A23L 29/212 |
| | | | 514/60 |
| 7,252,836 B2 * | 8/2007 | Brown .................... | A23L 33/21 |
| | | | 426/2 |
| 9,301,540 B2 | 4/2016 | Hopkins et al. | |
| 10,441,603 B2 | 10/2019 | Koenig et al. | |
| 2005/0031754 A1 * | 2/2005 | Maningat ................ | A23L 7/126 |
| | | | 426/549 |

(Continued)

FOREIGN PATENT DOCUMENTS

| | | | | |
|---|---|---|---|---|
| ES | 2331827 A1 * | 1/2010 | ........... | A23C 9/1206 |
| WO | 2018161077 A1 | 9/2018 | | |

OTHER PUBLICATIONS

Ahmadi, "New Prebiotics to Ameliorate High-Fat Diet-Induced Obesity and Diabetes via Modulation of Microbiome-Gut-Brain Axis", Diabetes, Jul. 2018, 67 (Supplement 1) (Year: 2018).*

(Continued)

*Primary Examiner* — Changqing Li
(74) *Attorney, Agent, or Firm* — Myers Bigel, P.A.

(57) ABSTRACT

Provided herein according to embodiments is a composition comprising polysaccharides isolated from sago or acorn for use as a dietary supplement or food additive. The composition is useful to improve gut health in a subject. Methods of extracting the polysaccharides and food products comprising the same are also provided.

20 Claims, 6 Drawing Sheets

(56)  References Cited

U.S. PATENT DOCUMENTS

| | | | | |
|---|---|---|---|---|
| 2006/0147465 | A1* | 7/2006 | Marshall | A61K 35/741 |
| | | | | 435/252.33 |
| 2013/0287874 | A1* | 10/2013 | Mercenier | A23C 9/1234 |
| | | | | 424/780 |
| 2013/0336931 | A1* | 12/2013 | Wadstrom | A61K 36/81 |
| | | | | 424/93.3 |
| 2017/0216328 | A1* | 8/2017 | Ritter | A61P 1/00 |

OTHER PUBLICATIONS

Topping, "Resistant starch as a prebiotic and synbiotic: state of the art", Proceedings of the Nutrition Society, 2003, 62, pp. 171-176 (Year: 2003).*

Arshad, "Resistant starch evaluation and in vitro fermentation of lemantak (native sago starch), for prebiotic assessment", International Food Research Journal, 2018, 25(3), pp. 951-957 (Year: 2018).*

Carlson, "Health effects and sources of prebiotic dietary fiber", Current Developments in Nutrition, 2018, 2(3), pp. 1-6 (Year: 2018).*

Tadayoni, "Isolation of bioactive polysaccharide from acorn and evaluation of its functional properties", International Journal of Biological Macromolecules, 2015, 72, pp. 179-184 (Year: 2015).*

Nagpal et al. "Prebiotics from acorn and sago prevent high-fat-diet-induced insulin resistance via microbiome-gut-brain axis modulation", Journal of Nutritional Biochemistry, 2019, 67, pp. 1-13 (Year: 2019).*

Albina, "Prebiotic Resistant Starch To Heal Leaky Gut And Support Colon Health" [Online], published Apr. 14, 2019, [retrieved on Apr. 24, 2019]. Retrieved from the Internet: <URL: https://victoriaalbina.com/resistant-starch/ > (Year: 2019).*

Correia, "The effect of starch isolation method on physical and functional properties of Portuguese nut starches. Ii. Q. rotundifolia Lam. and Q. suber Lam. acorns starches", Food Hydrocolloids, 2013, 30, pp. 448-455 (Year: 2013).*

Ahmadi, Shokouh , et al., "Dietary Polysaccharides in the Amelioration of Gut Microbiome Dysbiosis and Metabolic Diseases", Obesity & Control Therapies, 4(3), 2017, 1-25.

Ahmadi, Shokouh , et al., "Effects of different drying methods on the physicochemical properties and antioxidant activities of isolated acorn polysaccharides", LWT—Food Science and Technology, 100, 2019, 1-9.

Ahmadi, Shokouh , et al., "Prebiotics from acorn and sago prevent high-fat diet-induced insulin resistance via microbiome-gut-brain axis modulation", J. Nutritional Biochem., 67, 2019, 1-13.

Balakrishnan, Maya , et al., "Prebiotics, probiotics and digestive health", Current Opinion in Clinical Nutrition and Metabolic Care, 15(6), 2012, 580-585.

Barlow, Gillian M., et al., "Role of the Gut Microbiome in Obesity and Diabetes Mellitus", Nutr Clin Pract., 30(6), 2015, 787-797.

Bindels, Laure B., et al., "Non Digestible Oligosaccharides Modulate the Gut Microbiota to Control the Development of Leukemia and Associated Cachexia in Mice", PLoS One, 10(6): e0131009, 2015, 1-16.

Boler, Brittany M. Vester, et al., "In Vitro Fermentation Characteristics of Select Nondigestible Oligosaccharides by Infant Fecal Inocula", J. Agric. Food Chem., 61(9), 2013, 2109-2119.

Chen, Kang , et al., "Specific inulin-type fructan fibers protect against autoimmune diabetes by modulating gut immunity, barrier function, and microbiota homeostasis", Mol Nutr Food Res., 61(8), 1601006, 2017, 1-11.

Cho, Ilseung , et al., "The Human Microbiome: at the interface of health and disease", Nat Rev Genet. ; 13(4), 2012, 260-270.

Coll, Anthony P., et al., "The hypothalamus and metabolism: integrating signals to control energy and glucose homeostasis", Current Opinion in Pharmacology, 13(6), 2013, 970-976.

Costabile, Adele , et al., "Prebiotic Potential of a Maize-Based Soluble Fibre and Impact of Dose on the Human Gut Microbiota", PLoS One, 11(1), e0144457, 2016, 1-12.

Dahiya, Dinesh K., et al., "Gut Microbiota Modulation and Its Relationship with Obesity Using Prebiotic Fibers and Probiotics: A Review", Front. Microbiol., 8(563), 2017, 1-17.

De Vrese, Michael , et al., "Probiotics, Prebiotics, and Synbiotics", Food Biotechnology. Advances in Biochemical Engineering/Biotechnology, vol. 111. Springer, Berlin, Heidelberg., 2008, 1-66.

Everard, Amandine , et al., "Responses of Gut Microbiota and Glucose and Lipid Metabolism to Prebiotics in Genetic Obese and Diet-Induced Leptin-Resistant Mice", Diabetes, 60(11), 2011, 2775-2786.

Ferrario, Chiara , et al., "How to Feed the Mammalian Gut Microbiota: Bacterial and Metabolic Modulation by Dietary Fibers", Front. Microbiol., 8(1749), 2017, 1-11.

Furuta, Glenn T., et al., "Hypoxia-Inducible Factor 1-Dependent Induction of Intestinal Trefoil Factor Protects Barrier Function during Hypoxia", J Exp Med., 139(9), 2001, 1027-1034.

Heinken, Almut , et al., "Functional Metabolic Map of Faecalibacterium prausnitzii, a Beneficial Human Gut Microbe", J. Bacteriol., 196(18), 2017, 3289-3302.

Holscher, Hannah D., "Dietary fiber and prebiotics and the gastrointestinal microbiota", Gut Microbes, 8(2), 2017, 172-184.

Hosseini, Elham , et al., "Propionate as a health-promoting microbial metabolite in the human gut", Nutrition Reviews, 69(5), 2011, 245-258.

IHMP Research Network Consortium , "The Integrative Human Microbiome Project: Dynamic Analysis of Microbiome-Host Omics Profiles during Periods of Human Health and Disease", Cell Host & Microbe 16, 2014, 276-289.

Jain, Sanjay K., et al., "Design and development of hydrogel beads for targeted drug delivery to the colon", AAPS PharmSciTech, 8, 2007, E34-E41.

Kamada, Nobuhiko , et al., "Control of pathogens and pathobionts by the gut microbiota", Nat Immunol., 14, 2013, 865-890.

Kashyap, Purna C., et al., "Therapeutic implications of the gastrointestinal microbiome", Current Opinion in Pharmacology, 38, 2017, 90-96.

Kelly, Greg , "Inulin-Type Prebiotics: A Review (Part 2)", Alternative Medicine Review, 14(1), 2009, 36-55.

Lin, Chuan-Sheng , et al., "Impact of the Gut Microbiota, Prebiotics, and Probiotics on Human Health and Disease", Biomed J., 37, 2014, 259-268.

Long, Wenmin , et al., "Differential responses of gut microbiota to the same prebiotic formula in oligotrophic and eutrophic batch fermentation systems", Scientific Reports, 5, 13469, 2015, 1-11.

Lopez-Siles, Mireia , et al., "Faecalibacterium prausnitzii: from microbiology to diagnostics and prognostics", The ISME Journal, 11, 2017, 841-852.

Louis, Petra , et al., "How to Manipulate the Microbiota: Prebiotics", Adv Exp Med Biol., 902, 2016, 119-142.

Lynch, Susan V., et al., "The Human Intestinal Microbiome in Health and Disease", N Engl J Med, 375, 2016, 2369-2379.

Martí, Jose Manuel, et al., "Health and Disease Imprinted in the Time Variability of the Human Microbiome", mSystems, 2(2): e00144-16, 2017.

Miquel, S. , et al., "Faecalibacterium prausnitzii and human intestinal health", Current Opinion in Microbiology, 16(3), 2013, 255-261.

Nagpal, Ravinder , et al., "Gut Microbiome Composition in Nonhuman Primates Consuming a Western or Mediterranean Diet", Front. Nutr., 5(28), 2018, 1-9.

Nagpal, Ravinder , et al., "Human-origin probiotic cocktail increases short-chain fatty acid production via modulation of mice and human gut microbiome", Scientific Reports, 8(12649), 2018, 1-15.

Nagpal, Ravinder , et al., "Obesity-Linked Gut Microbiome Dysbiosis Associated with Derangements in Gut Permeability and Intestinal Cellular Homeostasis Independent of Diet", Diet. J Diabetes Res., 2018, 3462092, 2018, 1-10.

Nicolucci, Alissa C., et al., "Prebiotics Reduce Body Fat and Alter Intestinal Microbiota in Children Who Are Overweight or With Obesity", Gastroenterology, 153(3), 2017, 711-722.

(56) References Cited

OTHER PUBLICATIONS

Ohata, Atsushi , et al., "Short-chain fatty acids alter tight junction permeability in intestinal monolayer cells via ipoxygenase activation", Nutrition 21(7-8), 2005, 838-847.

Patel, Seema , et al., "The current trends and future perspectives of prebiotics research: a review", 3 Biotech, 2, 2012, 115-125.

Percy-Robb, I. W., et al., "Bile acids: a pH dependent antibacterial system in the gut?", Br Med J., 3(8), 1972, 813-815.

Pool-Zobel, Beatrice L., "Inulin-type fructans and reduction in colon cancer risk: review of experimental and human data", British J. Nutrition, 93(Suppl. 1), 2005, S73-S90.

Purwani, Endang Yuli, et al., "Fermentation RS3 derived from sago and rice starch with Clostridium butyricum BCC B2571 or Eubacterium rectale DSM 17629", Anaerobe, 18(1), 2012, 55-61.

Qamar, Tahir Rasool, et al., "Novel Combination of Prebiotics Galacto-Oligosaccharides and Inulin-Inhibited Aberrant Crypt Foci Formation and Biomarkers of Colon Cancer in Wistar Rats", Nutrients, 8(8), 465, 2016, 1-14.

Que, Fei , et al., "In vitro and vivo antioxidant activities of daylily flowers and the involvement of phenolic compounds", Asia Pac J Clin Nutr., 16(Suppl. 1), 2007, 196-203.

Reichardt, Nicole , et al., "Phylogenetic distribution of three pathways for propionate production within the human gut microbiota", The ISME Journal, 8, 2014, 1323-1335.

Roberfroid, Marcel B., et al., "Caloric Value of Inulin and Oligofructose", The Journal of Nutrition, 129(7), 1999, 1436S-1437S.

Rosen, Evan D., et al., "Adipocytes as regulators of energy balance and glucose homeostasis", Nature, 444, 2006, 847-853.

Segata, Nicola , et al., "Metagenomic biomarker discovery and explanation", Genome Biology, 12, R60, 2011, 1-18.

Shen, Li , et al., "Dietary Resistant Starch Increases Hypothalamic POMC Expression in Rats", Obesity, 17(1), 2009, 40-45.

Siew-Wai, Loo , et al., "Fermentation of Metroxylon sagu Resistant Starch Type III by Lactobacillus sp. and Bifidobacterium bifidum", J. Agric. Food Chem., 58(4), 2010, 2274-2278.

Slavin, Joanne , "Fiber and Prebiotics: Mechanisms and Health Benefits", Nutrients, 5(4),, 2013, 1417-1435.

Stanley, Sarah A., et al., "Bidirectional electromagnetic control of the hypothalamus regulates feeding and metabolism", Nature, 531(7596), 2016, 647-650.

Tadayoni, Mehrnoosh , et al., "Isolation of bioactive polysaccharide from acorn and evaluation of its functional properties", Int. J. Biol Macromol., 72, 2015, 179-184.

Takagi, Risa , et al., "A Single-Batch Fermentation System to Simulate Human Colonic Microbiota for High-Throughput Evaluation of Prebiotics", PLoS One, 11(8): e0160533, 2016, 1-16.

Taylor, Roy , "Insulin resistance and type 2 diabetes", Diabetes, 61(4), 2012, 778-779.

Tedelind, Sofia , et al., "Anti-inflammatory properties of the short-chain fatty acids acetate and propionate: A study with relevance to inflammatory bowel disease", World J Gastroenterol., 13(20), 2007, 2826-2832.

Tilg, Herbert , et al., "Prebiotics for obesity: a small light on the horizon?", Gut., 62, 2013, 1096-1097.

Van De Wouw, Marcel , et al., "Microbiota-Gut-Brain Axis: Modulator of Host Metabolism and Appetite", J Nutr., 147(5), 2017, 727-745.

Vigsnæs, Louise Kristine, et al., "In Vitro Fermentation of Sugar Beet Arabino-Oligosaccharides by Fecal Microbiota Obtained from Patients with Ulcerative Colitis To Selectively Stimulate the Growth of Bifidobacterium spp. and Lactobacillus spp.", Appl Environ Microbiol, 77(23), 2011, 8336-8344.

Viladomiu, Monica , et al., "Nutritional protective mechanisms against gut inflammation", The Journal of Nutritional Biochemistry, 24(6), 2013, 929-939.

Vinolo, Marco A.R., et al., "Regulation of inflammation by short chain fatty acids", Nutrients, 3(10), 2011, 858-876.

Wang, Dongdong , et al., "Inulin based glutathione-responsive delivery system for colon cancer treatment", International Journal of Biological Macromolecules, 111, 2018, 1264-1272.

Wang, Lirui , et al., "Methods to determine intestinal permeability and bacterial translocation during liver disease", J of Immunol. Methods, 421, 2015, 44-53.

Weitkunat, Karolin , et al., "Effects of dietary inulin on bacterial growth, short-chain fatty acid production and hepatic lipid metabolism in gnotobiotic mice", J Nutr Biochem., 26(9), 2015, 929-937.

Wilson, Bridgette , et al., "Prebiotic inulin-type fructans and galacto-oligosaccharides: definition, specificity, function, and application in gastrointestinal disorders", J Gastroenterol Hepatol., 32(Suppl. 1), 2017, 64-68.

Wu, Hao , et al., "Metformin alters the gut microbiome of individuals with treatment-naive type 2 diabetes, contributing to the therapeutic effects of the drug", Nature Medicine, 23(7), 2017, 850-858.

Yadav, Hariom , et al., "Beneficial Metabolic Effects of a Probiotic via Butyrate-induced GLP-1 Hormone Secretion", J Biol Chem., 288(35), 2013, 25088-25097.

Yadav, Hariom , et al., "Gut Microbiome Derived Metabolites to Regulate Energy Homeostasis: How Microbiome Talks to Host", Metabolomics, 6:e150, 2016.

Yadav, Hariom , et al., "Protection from Obesity and Diabetes by Blockade of TGF-β/Smad3 Signaling", Cell Metabolism, 14(1), 2011, 67-79.

Yadav, Hariom , et al., "TGF-β1/Smad3 Pathway Targets PP2A-AMPK-FoxO1 Signaling to Regulate Hepatic Gluconeogenesis", J. of Bio. Chem., 292(8), 2017, 3420-3432.

Binienda, Agata, et al., "Dietary Carbohydrates and Lipids in the Pathogenesis of Leaky Gut Syndrome: An Overview", International Journal of Molecular Sciences 21, 8368, 2020 (17 pages).

Paray, Bilal Ahmad, et al., "Leaky Gut and Autoimmunity: An Intricate Balance in Individuals Health and the Diseased State", International Journal of Molecular Sciences 21, 9770, 2020 (12 pages).

Pham, Van T., et al., "The effects of fermentation products of prebiotic fibres on gut barrier and immune functions in vitro", PeerJ 6:e5288, 2018 (22 pages).

Tsai, Yu-Ling, et al., "Probiotics, prebiotics and amelioration of diseases", Journal of Biomedical Science 26:3, 2019 (8 pages).

* cited by examiner a b

COMPOSITIONS USEFUL FOR DIETARY SUPPLEMENTS

CROSS-REFERENCE TO RELATED APPLICATIONS

This application claims the benefit of U.S. Provisional Application Ser. No. 62/916,622, filed Oct. 17, 2019, the entire contents of which is hereby incorporated by reference.

STATEMENT OF GOVERNMENT FUNDING

This invention was made with government support under Department of Defense funding W81XWH-18-1-0118, R01AG018915, and Wake Forest Clinical and Translational Science Institute (WF CTSI) funded through NIH Grant Award Number UL1TR001420. The United States government has certain rights in the invention.

BACKGROUND

Although the precise mechanisms that may trigger low-grade inflammation are still under study, increased gut permeability ("leaky gut") can allow non-selective diffusion of dietary and microbial antigens from the gut lumen, which may promote inflammatory response in the local (gut mucosa) and systemic immune systems. Emerging evidence suggests that detrimental perturbations in gut microbiome (dysbiosis) are associated with leaky gut, inflammation and poor health outcomes in older adults, indicating that gut therapies targeted to modulate the microbiome may ameliorate aging-related leaky gut and inflammation.

Gut permeability is normally tightly-controlled with intestinal barriers like tight junction proteins and a mucus layer. The mucus layer functions as a physical barrier to separate gut microbes and host cells, and protects from leaking and invading pathogens and antigens. The intestinal mucus layer covers the epithelial cells by making a viscoelastic gel layer, which is synthesized by goblet cells. Intestinal goblet cells are interspersed between epithelial cells on the villi of intestinal lumen and constantly secrete mucins to form the mucus layer. Mucin 2 (Muc2) is the major mucin secreted from intestinal goblet cells that forms major part of mucus layer in the gut, and it is known to protect leaky gut and invasion of microbes. Muc2 knockout (KO) mice develop colitis with a dramatic inflammatory gut mucosa that is linked to significant decreased thickness of mucus layer. The resulting thin mucus layer allows microbes of the gut to invade intestinal epithelial cells, activating an inflammatory response in immune cells. Similarly, the mucus layer thickness is dramatically reduced in the gut of older adults, and this is linked with increased leaky gut and inflammation. This evidences that the mucus layer plays an important role in regulating aging-related leaky gut and inflammation, and developing gut microbiota modulators that can promote mucin production can be beneficial to ameliorate aging-related leaky gut and inflammation.

Despite the growing acceptance of the importance of the gut barrier in diseases, knowledge of the underlying mechanism(s) that reinforce the barrier when faced with stressors is incomplete, and viable and practical strategies for pharmacologic modulation of the gut barrier remain unrealized. See WO 2018/161077 to Ghosh et al.

SUMMARY

Provided herein according to embodiments is a composition comprising polysaccharides isolated from sago or acorn for use as a dietary supplement or food additive. In some embodiments, the polysaccharides are present in the composition in an amount effective to improve gut health in a subject (e.g., a human or non-human mammalian subject).

In some embodiments, the composition is provided in a nutritionally acceptable carrier. In some embodiments, the carrier comprises a food product. In some embodiments, the composition is provided in a tablet or capsule suitable for enteral (e.g., oral) administration.

Also provided is a method of improving gut health in a mammalian subject in need thereof, comprising administering to the subject an effective amount of a composition taught herein, wherein said administering is by enteral administration.

Further provided is a method of making a food product comprising adding to ingredients of the food product a composition as taught herein.

In some embodiments, the food product is a dairy product such as milk, cheese, or yogurt. In some embodiments, the food product further comprises a probiotic (e.g. a *Lactobacillus* sp.).

In some embodiments, the food product is a yogurt comprising from 1, 2 or 3% to 8, 10 or 12% w/v of the polysaccharides isolated from sago (e.g., approximately 5% w/v).

Also provided is a yogurt comprising: from 0.1, 0.5, 1, 2 or 3% to 8, 10 or 12% w/v of the polysaccharides isolated from sago (e.g., approximately 5% w/v); from 0.1 or 0.15 to 0.2 or 0.25% w/v pectin; and from $10^7$ to $10^9$ CFU/mL probiotic lactobacillus strain(s).

Further provided is a method of extracting polysaccharides from sago, said method comprising: a) suspending sago in water to provided suspended sago (e.g., at a ratio of approximately 1:20 w/v); b) boiling the suspended sago, optionally while stirring (e.g., from 1, 2 or 5 to 10, 15 or 20 minutes); c) autoclaving the suspended sago (e.g., at approximately 121° C., 1.2 atm, for 1 h); d) cooling the suspended sago to provide a cooled suspended sago and incubating the cooled suspended sago a temperature of from 2 to 10 degrees Celsius (e.g. 4 degrees Celsius) and for a time of from 6 to 48 hours (e.g. 10, 15 or 20 to 30 or 48 hours); e) adding hydrolyzing enzymes to the suspended sago (e.g. alpha-amylase and pullulanase microbial) and incubating the suspended sago (e.g. for 6 to 48 hours (e.g. 10, 15 or 20 to 30 or 48 hours) at a temperature of approximately 70 degrees Celsius), optionally with mechanical agitation (e.g. with a shaker); f) separating non-soluble starches (e.g. by centrifugation) of the suspended sago and collecting the supernatant containing polysaccharides; and g) optionally, freeze drying supernatant, to thereby extract the polysaccharides from sago.

In some embodiments, the method provides a transparent composition comprising the polysaccharides useful as a food additive.

BRIEF DESCRIPTION OF THE DRAWINGS

FIG. 2. Effects of inoculation of prebiotics (inulin, acorn and sago) on the metabolic activity of microbiome in the feces of healthy versus diseased subjects. (panel a) Fecal pH of the fecal suspension from healthy and diseased subjects after 9 h incubation with (treatment) or without (control) prebiotics. (panels b,c) Production of lactate, acetate, propionate and butyrate in the fecal suspension from healthy (b) and diseased (c) subjects after 9 h incubation with (treatment) or without (control) prebiotics. Values are presented as mean±SD/SEM of n=6 replicates per treatment group. $P^*<0.05$; $^{**}P<0.01$.

Figure 3:
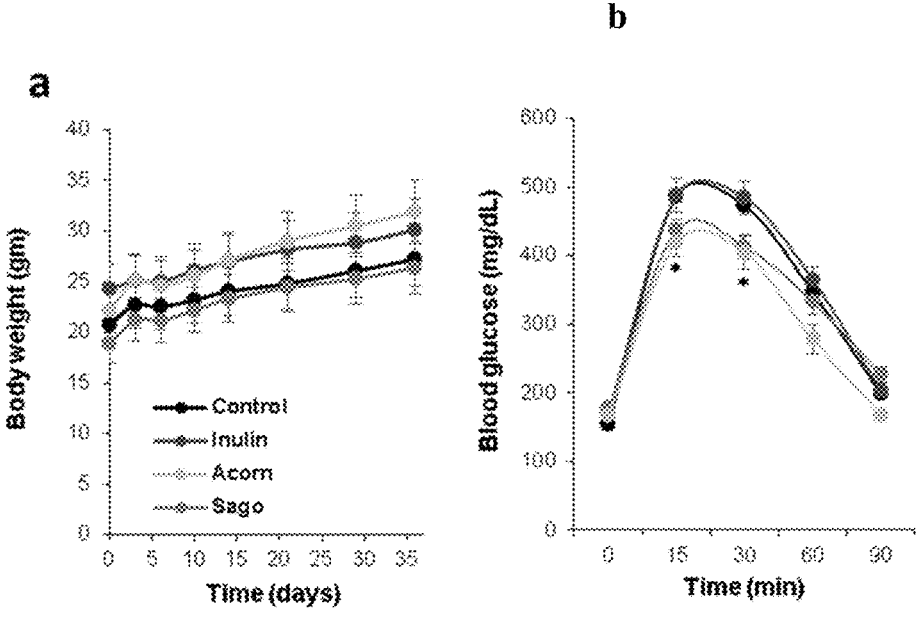
Figure 3:
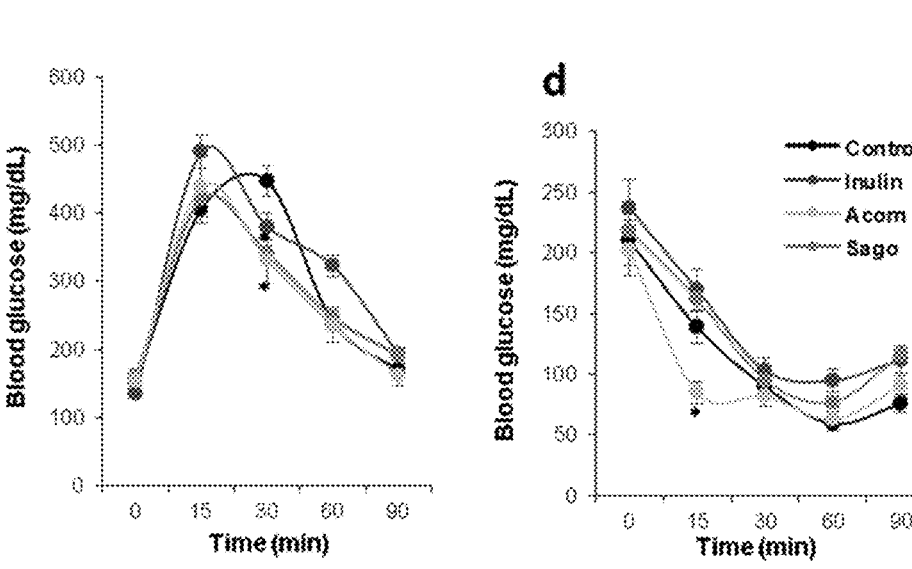

FIG. 3. Prebiotics prevent high-fat diet (HFD)-induced obesity in mice. (panel a) Body weight during HFD feeding with and without prebiotics up to 35 days/5 weeks. (panels b-d) Intraperitoneal glucose tolerance test (IPGTT; b), oral glucose tolerance tests (OGTT; c) and intraperitoneal insulin tolerance test (IPITT; d) in prebiotics-fed and control mice after 5 weeks of intervention. Values are presented as mean±SD/SEM. $P^*<0.05$; $^{**}P<0.01$; NS: non-significant.

Figure 4:
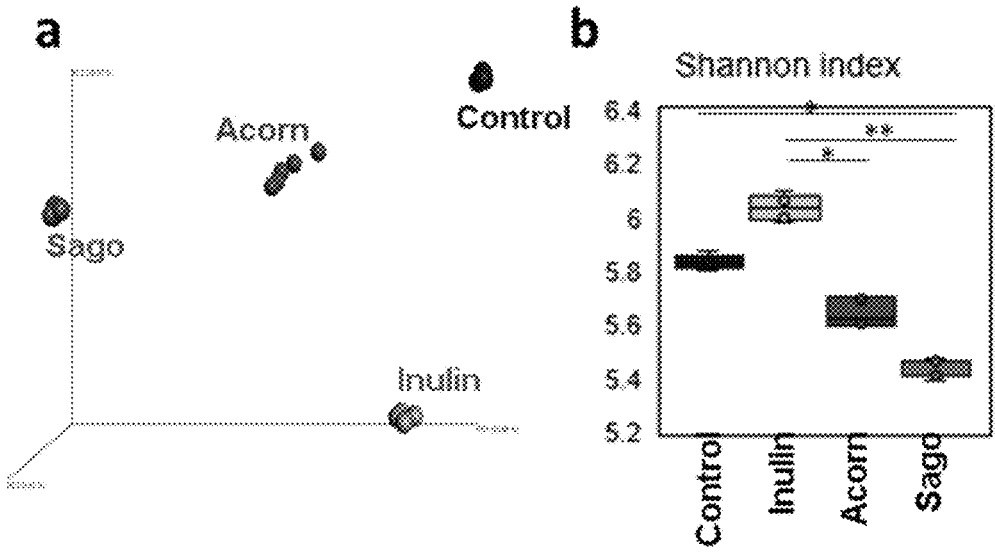

FIG. 4. Prebiotics modulate the diversity and composition of gut microbiome in HFD-fed mice. (panel a) PCoA analyses presenting β-diversity (weighted unifrac) of the gut microbiome in prebiotics-fed and control mice after 5 weeks of intervention. (panel b) Shannon index representing the α-diversity of gut microbiome in prebiotics-fed and control mice after 5 weeks of intervention. Values are presented as mean±SD/SEM. $P^*<0.05$; $^{**}P<0.01$.

Figure 5:
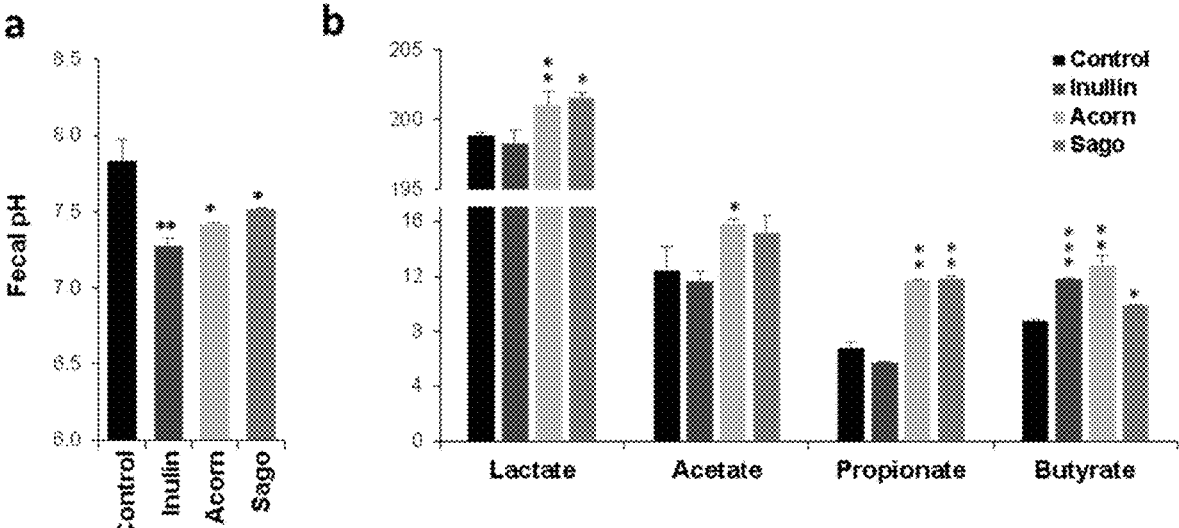

FIG. 5. Prebiotics modulate the metabolic activities of gut microbiome in HFD-fed mice. (panels a,b) Fecal pH (a) and levels of lactate, acetate, propionate and butyrate (b) in the feces of prebiotics-fed and control mice after 5 weeks of intervention. Values are presented as mean±SD/SEM. $P^*<0.05$; $^{}P<0.01$; $^{*}P<0.001$.

Figure 6:
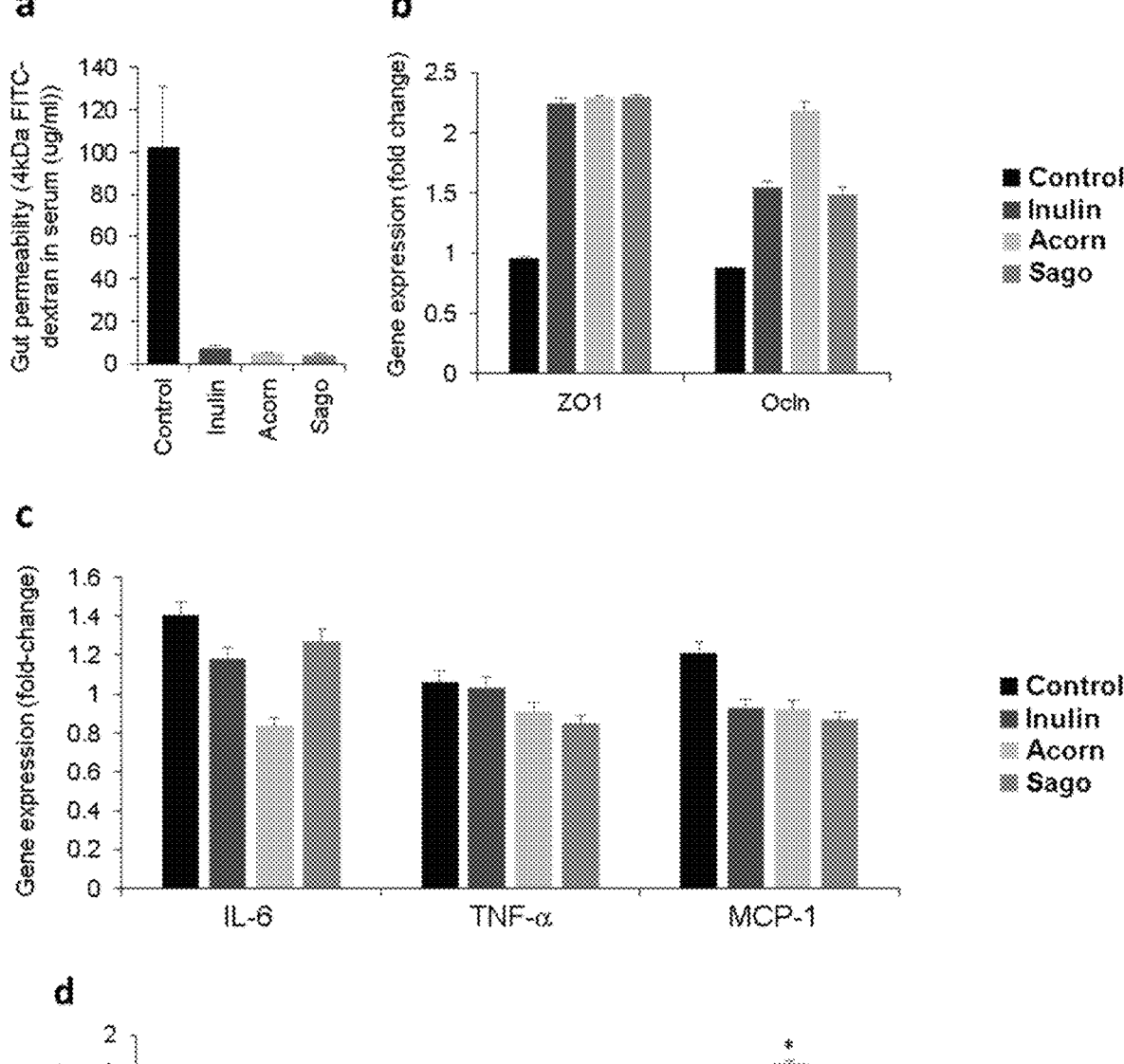

FIG. 6. Prebiotics ameliorate gut permeability, reduce inflammation and modulate gut-brain axis. (panel a) Gut permeability (in terms of the diffusion of 4 kDa FITC dextran from gut to blood circulation) in prebiotics-fed and control mice after 5 weeks of intervention. (panel b) Zonulin-1 (ZO-1) and Occludin (Ocln) mRNA expression in prebiotics-fed and control mice after 5 weeks of intervention. (panel c) Gene (mRNA) expression of inflammatory markers including Interleukine-6 (IL-6), tumor necrosis factor-alpha (TNF-α) and chemokine (C—C motif) ligand 2/monocyte chemoattractant protein 1 (Ccl2/MCP1) in prebiotics-fed and control mice after 5 weeks of intervention. (panel d) Gene (mRNA) expression of Agouti related protein (AgRP), neuropeptide Y (NPY) and Pro-opiomelanocortin (POMC) in the hypothalamus of (mRNA). Values are presented as mean±SD/SEM. $P^*<0.05$; $^{}P<0.01$; $^{*}P<0.001$.

Figure 7:
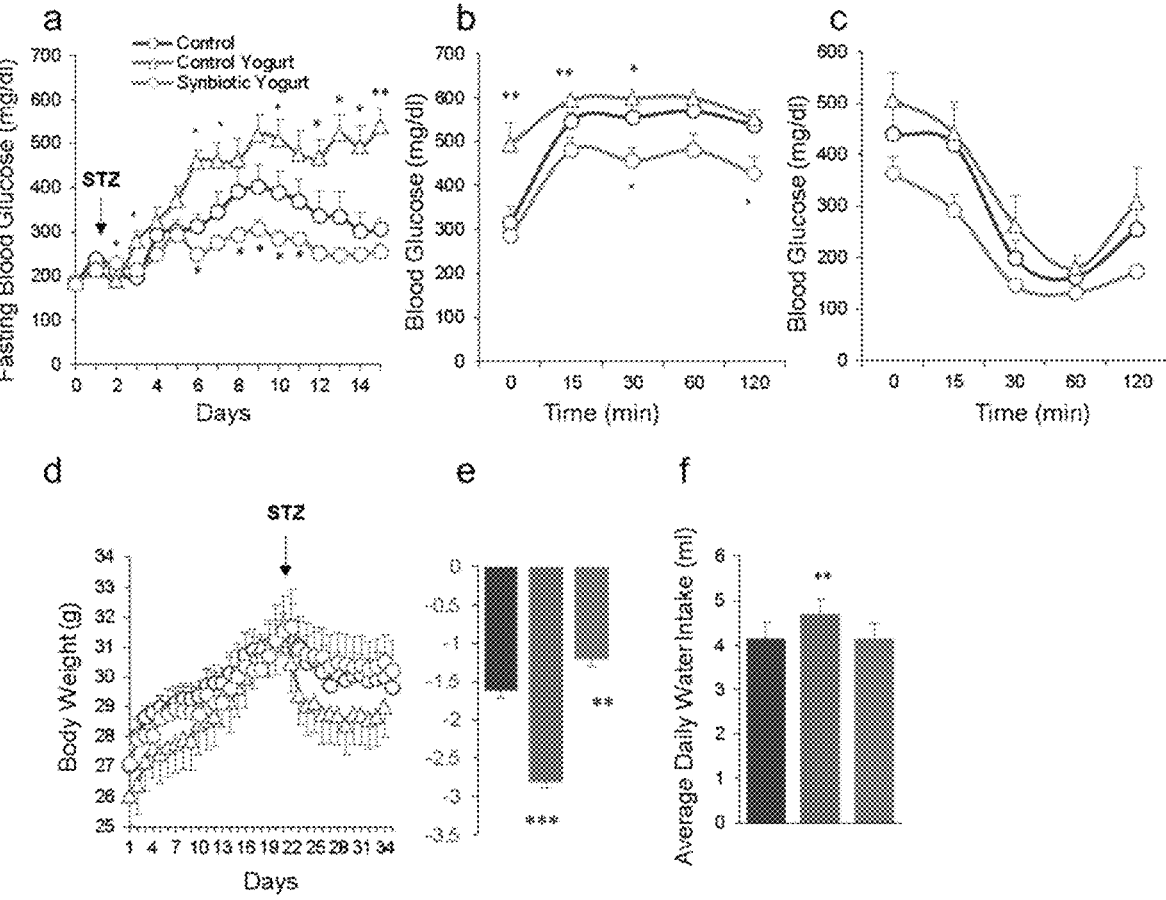

FIG. 7. Synbiotic yogurt ameliorates type-2 diabetes in mice. (panel 1) There were no significant differences in fasting blood glucose (FBG) in any of the groups due to HFD alone (before STZ). After STZ, the FBG was significantly lower in the synbiotic yogurt-fed mice (P<0.001). Although there were no significant differences during Week 1 (P=0.125; Figure), weekly sub-analysis revealed that there were significant differences among the groups during Week 2, with the synbiotic yogurt-fed mice having the lowest average FBG (P<0.001). (panels b, c) At baseline, there were no significant differences in meal tolerance between the groups (P=0.956) or the AUC (P=0.703). After five weeks of HFD, the synbiotic yogurt-fed mice demonstrated a lower rise in glucose during the meal tolerance test (MTT), but there was not a significant difference among the groups (P=0.052); however, the AUC revealed a significant difference (P=0.011). (panel d) There were significant differences among the groups in daily body weight (BW) over the five-week study (P<0.001), with the control yogurt-fed mice having the lowest average. (panel e) The overall average change in daily BW was similar due to HFD alone (P=0.223), but was significantly different after STZ (P<0.001), with the control yogurt-fed mice exhibiting the largest decrease. (panel f) The average daily water intake was significantly different between the groups and the control-yogurt fed mice had the highest intake (P=0.019). The average food intake per day was similar between the groups (P=0.313) (data not shown).

DETAILED DESCRIPTION

The disclosures of all patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise.

As used herein, "and/or" and "/" refer to and encompass any and all possible combinations of one or more of the associated listed items, as well as the lack of combinations when interpreted in the alternative ("or").

The term "about" or "approximately" means that the recited number or value can vary by +/−20%.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

"Subject" as used herein generally refers to a mammalian subject, including both human subjects and non-human mammalian subjects (e.g., dog, cat, horse, etc.) for research and/or veterinary purposes. Subjects may be male or female and may be of any suitable age, including neonate, infant, juvenile, adolescent, adult, and geriatric subjects; however in some embodiments the subject is an adult or geriatric subject.

"Improving gut health" as used herein refers to any type of treatment that imparts a benefit to the gut health a subject, which may be useful for alleviating gastrointestinal conditions such as leaky gut, inflammation, high-fat-diet-induced obesity, type 2 diabetes, etc. Such improvements may be by decreasing gut permeability, lowering expression of inflammatory genets (e.g., IL-6, TNF-α, MCP-1) increasing gut biome β-diversity, increasing the number of bacterial species associated with a health gut (e.g., *Bacteriodetes, Prevotellaceae, Prevotella*, etc.), and/or decreasing bacterial species associated with diseased gut (e.g., Enterobacteriaceae, etc.)

"Leaky gut" as used herein refers to a condition in which the gut barrier is impaired by loosening of epithelial cell-cell junctions and/or thinning of the layer of mucin that covers the epithelium of the intestinal tract. An impaired gut barrier (i.e., leaky gut) may be a major contributor to the initiation and/or progression of various chronic diseases, which may also be associated with aging, including, but not limited to, metabolic endotoxemia, type II diabetes, fatty liver disease, obesity, atherosclerosis, inflammatory bowel diseases, Alzheimer's disease, Parkinson's disease, cardiovascular diseases, certain cancers, and other inflammatory diseases.

Polysaccharides may be isolated from sago or acorn (the nut of oaks and related trees) in accordance with the methods described herein in the Examples or in accordance with methods known in the art. See, e.g., U.S. Pat. No. 9,301,540 to Hopkins et al. Sago is a starch extracted from the pith of various tropical palm stems, such as that of *Metroxylon sagu*.

An example of a method of extracting polysaccharides from sago as taught herein may include one or more of: a) suspending sago in water to provided suspended sago (e.g., at a ratio of approximately 1:20 w/v); b) boiling the suspended sago, optionally while stirring (e.g., from 1, 2 or 5 to 10, 15 or 20 minutes); c) autoclaving the suspended sago (e.g., at approximately 121° C., 1.2 atm, for 1 h); d) cooling the suspended sago to provide a cooled suspended sago and incubating the cooled suspended sago a temperature of from 2 to 10 degrees Celsius (e.g., 4 degrees Celsius) and for a time of from 6 to 48 hours (e.g., 10, 15 or 20 to 30 or 48 hours); e) adding hydrolyzing enzymes to the suspended sago (e.g. alpha-amylase and pullulanase microbial) and incubating the suspended sago (e.g., for 6 to 48 hours (e.g. 10, 15 or 20 to 30 or 48 hours) at a temperature of approximately 70 degrees Celsius), optionally with mechanical agitation (e.g., with a shaker); f) separating non-soluble starches (e.g., by centrifugation) of the suspended sago and collecting the supernatant containing polysaccharides; and g) optionally, freeze drying supernatant to form a powdered extract. Such a method can advantageously form a transparent composition comprising the polysaccharides, which is useful as a food additive that will not adversely affect the natural color of the food.

Another aspect of the invention relates to a composition comprising the isolated polysaccharide and a pharmaceutically or nutritionally acceptable carrier. Suitable carriers may include, but are not limited to, excipients and diluents. Examples of suitable carriers include lactose, starch, glucose, methyl cellulose, magnesium stearate, mannitol, sorbitol and the like. Examples of suitable diluents include ethanol, glycerol and water (e.g., sterile or purified water).

The compositions may also comprise suitable binder(s), lubricant(s), suspending agent(s), coating agent(s), solubilizing agent(s), etc. Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like.

Preservatives, stabilizers, dyes and/or flavoring agents may be provided in the composition, if desired. Examples of preservatives include sodium benzoate, sorbic acid and esters of p-hydroxybenzoic acid. Antioxidants and suspending agents may be also used.

Nutritionally acceptable carriers, diluents and excipients include those suitable for human or animal consumption and that are used as standard in the food industry. Typical nutritionally acceptable carriers, diluents and excipients will be familiar to the skilled person in the art.

In some embodiments the composition is suitable to be administered orally, enterally or rectally. For example, the composition may be an edible composition in that it is suitable for human or animal consumption.

Another aspect of the invention relates to a prebiotic composition comprising the polysaccharides isolated from sago and/or acorn. As used herein, the term "prebiotic" means polysaccharides that are resistant to mammalian digestive enzymes, acidity and intestinal absorption, that are fermentable by gut microbiota, and that stimulate the growth of gut microbial communities associated with health benefits. See, e.g., U.S. Pat. No. 10,441,603 to Koenig et al. The prebiotic composition may be an orally administrable composition comprising the polysaccharides. The prebiotic composition may contain other ingredients, and may be provided in a suitable oral dosage form, e.g., in the form of a tablet, capsule or powder.

A further aspect of the invention relates to food products, dietary supplements, nutraceuticals, nutritional formulae, drinks and medicaments comprising the polysaccharides isolated from sago and/or acorn, and use thereof. Examples of specific food products that are applicable to the present invention include milk-based products such as ice cream, ready-to-eat desserts and/or baked products, powders for re-constitution with, e.g., milk or water, chocolate milk drinks, malt drinks, smoothies, baby formula, ready-to-eat dishes, instant dishes or drinks for humans or food compositions representing a complete or a partial diet intended for pets or livestock, chewing gum, etc.

An example food product is a yogurt comprising from 0.1, 0.5, 1, 2 or 3% to 8, 10 or 12% weight/volume of the polysaccharides isolated from sago (e.g., approximately 5% w/v). The yogurt may also comprise from 0.1 or 0.15 to 0.2 or 0.25% weight/volume pectin. In some embodiments, the yogurt further comprises a probiotic such as lactobacillus strain(s) (e.g. at a concentration of from $10^7$ to $10^9$ CFU/mL). An example preparation of such a yogurt is described below in Example 2.

Example probiotic strains include, but are not limited to, *Lactobacillus* strains such as *L. rhamnosus* (e.g. D7.5, D6.1), *L. paracasei* (e.g. D3.5), and *L. plantarum* (e.g. D13.4, D4.4), *Streptococcus* strains, *Bifidobacterium* strains, Enterococci strains, etc. See, e.g., U.S. Pat. No. 9,540,609 to Burton et al.; Nagpal et al., Sci Rep. 2018; 8: 12649.

The present invention is explained in greater detail in the following non-limiting examples.

EXAMPLES

Example 1: Prebiotics from Acorn and Sago Prevent High-Fat Diet-Induced Insulin Resistance Via Microbiome-Gut-Brain Axis Modulation Role of gut microbiome in obesity and type 2 diabetes (T2D) became apparent from several independent studies, indicating that gut microbiome modulators like prebiotics may improve microbiome perturbations (dysbiosis) to ameliorate metabolic derangements. Water soluble, non-digestible polysaccharides were isolated from five plant based foods (acorn, *quinoa*, sunflower, pumpkin and sago seeds) and their impact on human fecal microbiome and amelioration of high fat diet (HFD)-induced obesity/T2D was assessed in mice. During polysaccharide isolation, purification, biochemical and digestion resistance characterization, and fermentation pattern by human fecal microbiome, acorn- and sago-derived prebiotics were selected (on the basis of relatively higher purity and yield and lower protein contamination) and their effects examined in comparison to inulin.

Prebiotics treatments in human fecal microbiome culture system not only preserve microbial diversity but also appear to foster beneficial bacteria and short-chain fatty acids (SCFAs). Feeding of acorn- and sago-derived prebiotics ameliorates HFD-induced glucose intolerance and insulin resistance in mice, with effects comparatively superior to those seen in inulin-fed mice. Feeding of both of novel prebiotics as well as inulin increases SCFAs levels in the mouse gut.

Interestingly, gut hyperpermeability and mucosal inflammatory markers were significantly reduced upon prebiotics feeding in HFD-fed mice. Hypothalamic energy signaling in terms of increased expression of pro-opiomelanocortin, was also modulated by prebiotics administration. Results demonstrate that these prebiotics can ameliorate HFD-induced defects in glucose metabolism via positive modulation of gut-microbiome-brain axis and hence could be useful in preventing/treating diet-induced obesity/T2D.

The relationship between gut microbiome and human health became one of the most significant scientific discoveries of the past decade [1, 2]. The complex composition of gut microbial community influences host health and vice-versa [3]. Gut microbiome perturbations (dysbiosis) have been associated with several human diseases including obesity and diabetes [4]. Therefore, manipulation of gut microbiome can ameliorate host health and disease pathology, remain of great interest to develop therapeutic strategies against such maladies [5]. However, diet is one of the major manipulator of microbial species living in the gut and their metabolic activities via involving fermentation of non-digestible dietary fibers [6]. Produced secondary metabolites after microbial fermentation remain major denominators to define interactions between microbiome and host cellular systems [7]. Dietary fibers and several non-digestible oligo- or poly-saccharides are known to be one of the important microbiome modulators that are fermented by gut microbes [8]. These polysaccharides are neither digestible nor absorbable by mammalian gut, hence reach to lower part of intestine wherein these serve as food/substrate for microbial fermentation and promote the growth and activities of certain health beneficial bacterial communities [9]. Such polysaccharides are generally termed as 'prebiotics', however according to recent definition, they must follow three criteria; 1) resistant to mammalian digestive enzymes, acidity and intestinal absorption, 2) fermentable by gut microbiota and 3) growth stimulator of selective gut microbial communities associated with health benefits [10]. Consumption of prebiotics in early and adult life lead to increase production of certain fermentative metabolites like short chain fatty acids (SCFAs i.e. acetate, propionate and butyrate) that exert health beneficial effects to the host [11, 12]. Prebiotics are heterogeneous and complex polysaccharides and are thereby defined either by the origin and/or chemical composition of their single sugar moieties, both of which can impact the pattern of their microbial fermentation as well as microbial consumers of these complex carbohydrates, thereby imparting unique effects on the gut microbiome [13, 14]. Although, the most commonly studied prebiotics are inulin-type (e.g., fructo-oligosaccharides, galacto-oligosaccharides, etc.) [9, 15-17], however newly developed prebiotics are highly warranted to devise strategies specific for increasing demand of prebiotics use in different sectors, as well as trailer according to different pathological conditions to manipulate gut microbiome and benefit host.

Polysaccharides from diverse natural sources have been isolated and studied for health beneficial impact in animal and human studies [18]. Prebiotics such as inulin are known to exhibit anti-carcinogenic effects against colon cancer [19-21]. Prebiotic pectic-oligosachairdes have been found to modulate the gut microbiome (increased *Bacteroides Prevotella* groups) with enhanced short-chain fatty acid (SCFAs) production (especially acetate and propionate) in human feces [22]. Oligofructose (Orafti, Tienen, Belgium) prebiotics feeding to obese and diabetic mice has been shown to augment beneficial gut microbiome signature along with improvements in glucose homeostasis, leptin sensitivity, inflammatory status, intestinal turnover and target enteroendocrine cell activity [23]. Short-term feeding of Promitor™ Soluble Corn Fibre (a maize-derived source of dietary fiber) boosted Bifidobacteria population in the gut [24]. Altogether, these studies evidence potent beneficial roles of prebiotics in wide-spectrum health conditions. However, comprehensive effects of prebiotic formulations on host metabolism and the mechanisms underlying these effects remain largely unclear. Therefore, exploration of novel and more defined prebiotics remains requisite and could facilitate the development of more efficient remedies to ameliorate obesity/diabetes and other human health problems.

In-vitro fermentation systems are becoming popular models to define the direct impact of prebiotics interventions on gut microbiome by saving time, efforts and money, in prior and/or parallel to next level physiological relevance. Recently, Long et al. [25] defined the effects of media conditions and prebiotic fermentation on human gut microbiome using in-vitro culture. Vigsnæs et al. [26] showed that sugar beet arabino-oligosaccharides stimulated dramatic changes in gut microbiome by stimulating the growth of *Bifidobacterium* spp. and *Lactobacillus* spp. in an in-vitro fermentation system of ulcerative colitis patient's feces. Takagi et al. [27] validated high-throughput screening of prebiotics using single-batch fermentation system to analyze the effects on gut microbiome. Recently, we also validated this system to demonstrate the effect of a human-origin probiotic cocktail on the microbiome composition and organic acids levels in human feces [28]. In the present study, we isolate and characterize novel prebiotics from common plant-based food ingredients and analyze their influence on human fecal microbiome and its metabolic activities in comparison to one of the most-widely studied prebiotics namely, inulin. In addition, we demonstrate several beneficial effects of selected prebiotics in the prevention of high-fat diet (HFD)-induced obesity and diabetes in mice via modulating microbiome-gut-brain axis.

Results

Yield and purification of water-soluble polysaccharides. We extracted total polysaccharides from acorns, pumpkin seeds, quinoa, sunflower seeds and sago, and found that the total polysaccharide yield was highest in sago (17.5% of dry weight) followed by acorns (5%), quinoa (3%), sunflower seeds (0.2%) and pumpkin seeds (0.1%) (data not shown). In terms of the total sugar content in the dry weight of total extracted polysaccharides, the sago extracts were found to possess highest purified sugars (99.8%) followed by quinoa (99.1%), acorns (98.7%), sunflower seeds (69%) and pumpkin seeds (51.2%). Protein content was found to be highest in sunflower seeds (7.5%), followed by pumpkin seeds (6%), acorns (3%) with no detectable protein contamination in quinoa and sago extracts. However, total polyphenolic compounds were lowest in sago extract (0.09%) with increasing trend in quinoa (0.17%), sunflower seeds (0.27%), acorns (0.3%) and pumpkin seeds (0.57%). Interestingly, the polyphenolic contents in these extracts directly correlated with the high antioxidant activity of these extracts (data not shown).

Prebiotic features of newly isolated polysaccharides. Upon analyzing the carbohydrate digestion pattern of different polysaccharide extracts using simulated gastric fluid (pH 1.2), simulated intestinal fluid (pH 7.4 with α-amylase) and mixture of simulated gastric and intestinal fluids (pH 4.5) [29], we found that the sago polysaccharide extract was digested at highest rate upon digestion in simulated gastric juice, while the digestion rate in simulated intestinal fluids was highest for acorn extract (data not shown). Interestingly, mixture of simulated gastric and intestinal juice did not exhibit any differential effects on digestion of these polysaccharide extracts, suggesting that these differences might be due to different pH of gastric versus intestinal fluids. Enzyme activities viz. α-amylase, however, did not show any significant difference among five polysaccharide extracts (data not shown).

Figure 1:
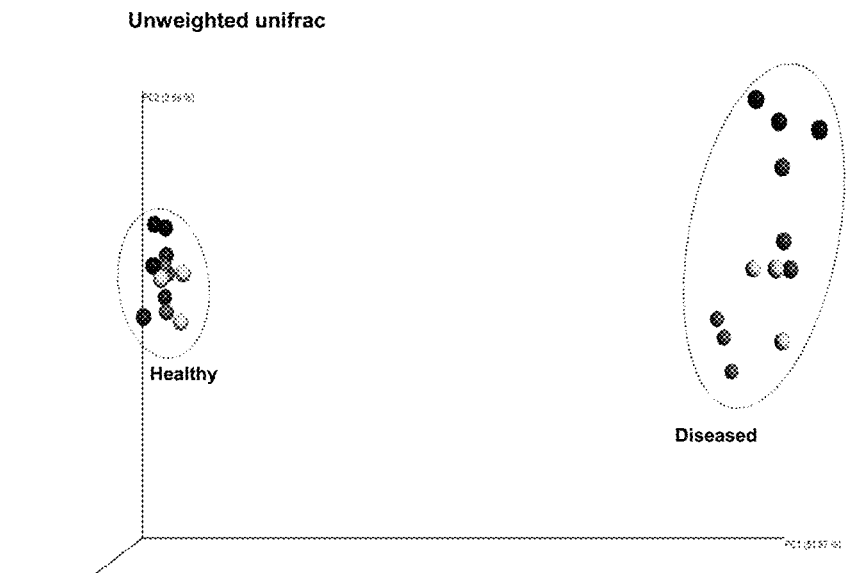
FIG. 1. Effect of inoculation of prebiotics (inulin, acorn and sago) on the microbiome diversity and composition in the feces of healthy versus diseased (heart attack patients) subjects. (panels a,b) PCoA analyses (a: unweighted unifrac; b: weighted unifrac) representing the α-diversity of microbiome; (panel c) Shannon index representing the α-diversity of microbiome. Values are presented as mean±SD/SEM. *$P<0.05$;  $P<0.01$; *$P<0.001$.
Figure 1:
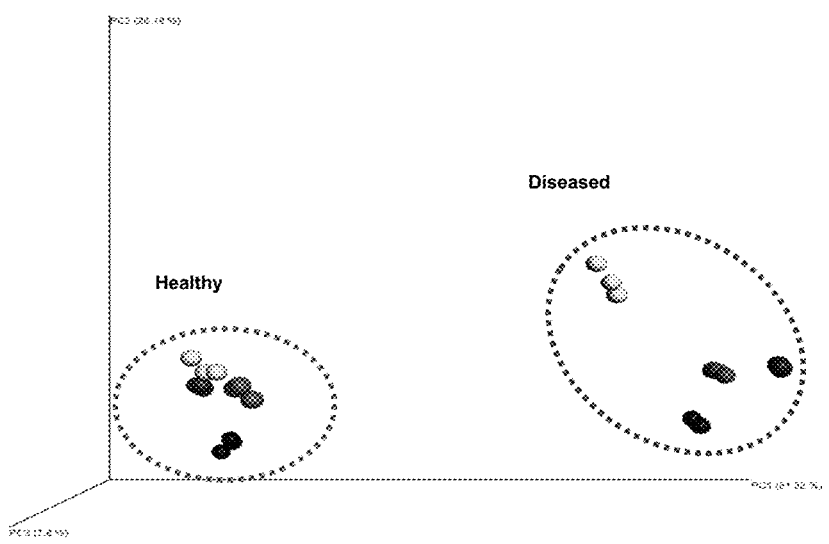
Figure 1:
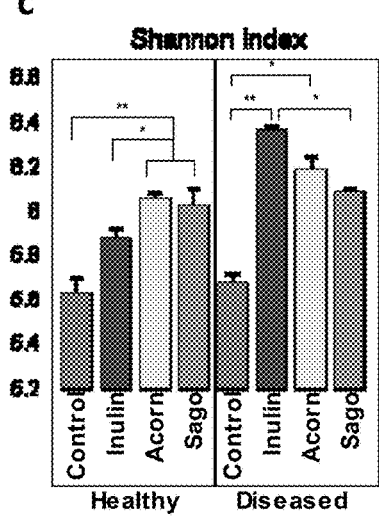

Influence of novel prebiotics on fecal microbiome of healthy and diseased human subjects. On the basis of our preliminary analyses of prebiotic yield, purity, sugar content and digestibility patterns, we selected acorn and sago prebiotics to further investigate their impact on human fecal microbiome using an ex-vivo anaerobic fecal slurry culture system and compared their effects to those of inulin. In addition, we also designed our study in a way to approximately distinguish the effects of selected prebiotics on gut microbiome in healthy versus diseased (heart failure patients) subjects. Principal co-ordinate analysis (PCoA) of microbial β-diversity (weighted and unweighted unifrac) indicated that the prebiotics treatments induced increased β-diversity in diseased fecal microbiome, while no significant change in β-diversity was seen in healthy fecal microbiome (FIG. 1, panels a,b). Alpha-diversity in terms of Shannon index was significantly higher in all prebiotics treatments in both healthy and diseased fecal microbiome (FIG. 1, panel c); however, other alpha-diversity indices like phylogenetic degree (PD) tree, number of observed OTUs, and Chao1 were significantly increased in diseased fecal microbiome samples, with minor elevation in healthy feces (data not shown), suggesting that prebiotics intervention modulated the gut microbial diversity more prominently in diseased sample as compared to healthy microbial ecosystem. Interestingly, acorn prebiotic significantly increased *Bacteriodetes* in healthy fecal microbiome, while both acorns and sago prebiotics significantly increased *Bacteriodetes* and decreased *Firmicutes* in diseased microbiome (data not shown). However, Proteobacteria abundance was significantly decreased upon all the prebiotic treatments compared to control (non-treated) (data not shown). Family Prevotellaceae and genus *Prevotella* were dominant in healthy feces and were increased further upon inulin and sago treatments, while diseased feces were enriched with Bacteroidaceae and *Bacteroides* that were increased after prebiotics treatments (data not shown). Abundance of unclassified genera belonging to family Enterobacteriaceae was significantly higher in diseased feces compared to healthy samples, but decreased upon prebiotics treatments (data not shown) in both types of fecal cultures. Linear discrimination analysis (LDA) shows that the inulin treatment induced minor changes including significantly increased *Firmicutes* (e.g., *Dialister* and *Megasphaera*) in healthy fecal microbiome, while this treatment dramatically changed the microbiome signature in diseased feces by increasing *Firmicutes* groups viz. *Dialister, Megasphaera, Phascoarctobacterium, Faecalibacterium, Blautia, Clostridium, Streptococcus* and *Enterococcus*, as well as Actinobacteria viz. *Bifidobacterium*. Acorns prebiotics treatment increased *Bacteriodetes* members viz. *Bacteroides* and

*Prevotella; Firmicutes* member *Fecalibacterium*, and Proteobacteria groups viz. *Sutterella* and *Succinovibrio* in healthy fecal microbiome (data not shown), while it increased *Firmicutes* viz. *Oscillospira, Catenibacterium* and *Sutterella* in diseased microbiome (data not shown). The most significant changes in microbiome signature were noticed in sago prebiotics treated healthy feces, where *Firmicutes* including *Bulleidia, Clostridia, Ruminococcus Streptococcaceae*, and *Lactococcus*, and Actinobacteria including Bifidobacteria and *Collinsella*, and *Methanobrevibacter* were significantly increased, while *Firmicutes* member *Lactobacillus* and *Bacteriodetes* members *Paraprevotella, Butyricomonas, Parabacteriodes* and S24_7 were increased in diseased feces (data not shown). In addition, all the prebiotics significantly decreased Enterobacteriales, unclassified *Clostridiales, Trabulsiella, Enterobacter* and *Anaerostipes* (data not shown).

Figure 2:
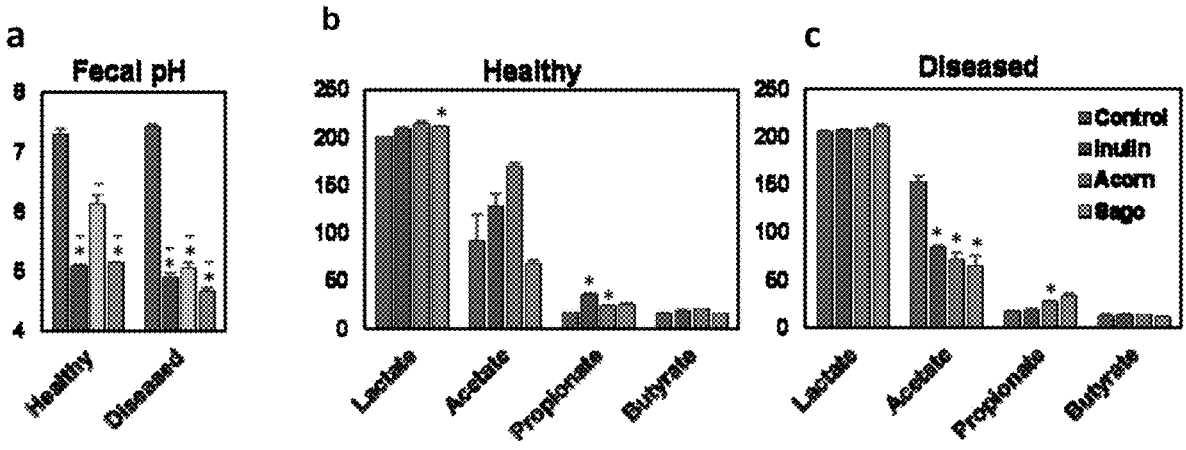

Inoculation of prebiotics decreases pH and enhances SCFAs levels in the feces of healthy and diseased human subjects. Simple and complex non-digestible polysaccharides primarily go through gut microbiota fermentation wherein gut microbes metabolize these substrates and produce diverse metabolites, mainly organic acids including lactate, acetate, propionate, butyrate, etc. [30, 31]. We assessed the prebiotic fermentative potential of healthy versus diseased human fecal microbiome in fecal culture system (ex-vivo) to produce organic acids and found a significant reduction in the pH of fecal slurry of both healthy and diseased donors after 9 h of incubation with each of the prebiotics tested (FIG. 2, panel a). Further assessment of SCFAs including lactate, acetate, propionate and butyrate produced upon fermentation of prebiotics by human fecal microbiome revealed that the acorns increased lactate, while sago prebiotics increased acetate production compared non-treated controls in healthy fecal microbiome (FIG. 2, panel b). While no significant effect of any of the prebiotics treatments on lactate production was observed in diseased fecal microbiome, acetate production was significantly decreased in these fecal microbiome (FIG. 2, panel c). Interestingly, acorns prebiotics increased propionate production in both healthy and diseased fecal microbiome cultures, while sago prebiotics increase propionate only in diseased feces, whereas inulin treatment increased propionate only in healthy fecal microbiome (FIG. 2, panels b,c). No significant changes were seen in butyrate production in healthy and diseased microbiome fecal cultures upon prebiotics intervention compared to control (FIG. 2, panels b,c). Further correlation analysis of gut microbiome, pH and SCFAs content in healthy fecal specimen suggested that increased lactate production was primarily attributed to sago prebiotics that was also associated with increased abundance of *Streptococcus*, Actinobacteria and *Lactococcus* (data not shown). Propionate production was significantly increased by inulin and acorns and was correlated with increased abundance of *Lactobacillus* in inulin; however, *Bacteriodetes, Prevotella* and *Faecalbacterium* were positively associated with propionate but insignificantly. In diseased fecal microbiome, acetate production was decreased in all the prebiotics treated groups and was correlated with *Rikenellaceae* (data not shown). Increased propionate levels primarily in acorn prebiotics were correlated with *Bacteroidetes, Bacteroides, Parabacteroides,* S24_7, *Rikenellaceae, Paraprevotella*, and *Sutterella* (data not shown).

Prebiotics prevent development of glucose intolerance and insulin resistance in HFD-fed mice. To examine the effect of prebiotics on the features of host glucose metabolism, we fed mice with selected prebiotics (acorns and sago)

supplemented (5%) in high-fat diet (HFD) for 8 weeks. No notable differences were observed in body weight, total fat depots, and liver and quadriceps muscle weights (FIG. 3, panel a). However, interestingly, a faster clearance of glucose within 2 hrs during both intraperitoneal (i.p.) and oral glucose tolerance test (IPGTT and OGTT) was seen in both acorn and sago prebiotics fed mice (FIG. 3, panels b,c), as also further evident from a significantly decreased area under curve (AUC) of GTTs in acorn and sago fed mice (data not shown), thereby suggesting that both prebiotics prevented the progression of HFD-induced glucose intolerance (a prediabetes condition) in mice. In addition, a significantly faster decline/clearance of glucose in response to exogenous insulin (FIG. 3, panel d), with an increased AUC (data not shown), was also seen during insulin tolerance test (ITT) in mice fed with prebiotics, especially inulin and acorns, suggesting that prebiotics prevented development of HFD-induced insulin resistance (a hallmark of type 2 diabetes). No significant differences were seen in fasting blood glucose (data not shown) and food intake (data not shown) in prebiotics-fed versus control groups. In addition, calorie intake from HFD were also almost identical among all the groups, and in fact prebiotics fed mice consumed extra calories (data not shown), suggesting that small differences in calories might not account for differences in body weight and adiposity, however the source of calories and how these get digested may have larger effects. We also noted that white adipose tissue (epididymal/gonadal) cell size was smaller in prebiotics-fed (especially inulin and acorn) mice compared to control counterparts. In addition, each of the prebiotics significantly decreased fat accumulation in brown adipose tissue (supra-scapular) and liver (data not shown). Overall, these results suggest that these prebiotics prevented HFD-induced metabolic derangements i.e., glucose intolerance, insulin resistance and tissue fat accumulation in mice.

Prebiotics prevent gut microbiome dysbiosis in diet-induced obese (DIO) mice. Upon evaluating the impact of these novel prebiotics on HFD-induced gut microbiome dysbiosis in mice, we noted dramatic differences in the β-diversity (a measure of overall gut microbial diversity as revealed by the PCoA analysis) of gut microbiome in all of the prebiotics-fed mice as compared to control (non-treated) group, (FIG. 4, panel a), thereby clearly indicating that prebiotics significantly modulated the signatures of gut microbiome in these mice. Furthermore, α-diversity measures including PD whole tree, Chao1, observed OTUs and Shannon index significantly differed between prebiotics versus control groups (FIG. 4, panel b). Particularly, acorns and sago prebiotics-fed mice appeared to have lower indices of all these measures; however, these differences were associated with the expansion of Bacteroidetes and decline in Firmicutes abundance (data not shown). A significantly lower abundance of unclassified Clostridiales group was seen in inulin- and sago-fed groups, with no significant changes in acorns group (data not shown). Ruminococcaceae (specifically Oscillospira), Desulfovibrionaceae (genus Desulfovibrio) and Bilophila were lower in all of the prebiotics groups compared to control; however, S24_7 (a major Bacterioidetes family) was significantly higher especially in acorns- and sago-fed mice. Family Erysipelotrichaceae was significantly expanded in all the prebiotics-fed groups (data not shown). In addition, Lactobacilliaceae (Lactobacillus) and Verrucomicrobiaceae (Akkermensia) were higher in inulin-fed mice, while no significant changes in the abundance of these clades were seen in acorns- and sago prebiotics-fed mice (data not shown). Interestingly, linear discrimination analysis (LDA) using LefSe (LDA Effect Size) demonstrated higher abundance of Bifidobacteria, Mucispirilium, Enterococcus, Lactobacillus, Clostrium, Dorea and Ruminococcus genera are enriched in inulin-fed mice, while Bacteroides, Parabacteroides, S24_7, Lactococcus, Streptococcus and SMB53 abundance were enriched in sago-fed mice (data not shown). AF12 was only significantly higher in acorns-fed mice (data not shown).

While investigating the impact of prebiotics on metabolic function of gut microbiome, we found that the fecal pH was significantly decreased in all the prebiotics treated mice compared to control (FIG. 5, panel a). To find the contribution of prebiotics to produce organic acids or SCFAs via microbial fermentation, we found that acorns and sago prebiotics-fed mice had significantly higher fecal concentration of lactate. Acetate was also higher in acorns-fed mice, while no significant changes in SCFAs were observed in inulin-fed mice. Propionate levels were significantly higher in acorns- and sago-fed mice but not in inulin group. Interestingly, butyrate levels were higher in all the prebiotics-fed groups compared to control, with levels being highest in acorns-fed mice followed by inulin- and sago-fed groups (FIG. 5, panel b). Further analysis of correlation between fecal pH, SCFAs levels and microbiome groups indicated that higher lactate and propionate in acorns and sago groups were positively correlated with higher abundance of Bacteroidetes, S24_7, Rikenellaceae and Parabacteroids; lactate levels were negatively correlated with Proteobacteria, Mucispirilium, Akkermansia, Dorea and Enterococcus, while acetate and butyrate levels shared positive—albeit insignificant—correlation with Rikenellaceae and Parabacteroides (data not shown).

Prebiotics improve gut physiology with decreased intestinal permeability in diet-induced obese (DIO) mice. Mice fed with prebiotics had higher fecal frequency along with higher stool quantity and lower fecal water content (data not shown), suggesting overall functional improvements in gut physiology. Interestingly, we found that gut permeability (in-terms of the diffusion of 4-kDa-FITC (Fluorescein isothiocyanate)-dextran from gastrointestinal tract into the blood) was dramatically lower in mice fed with prebiotics compared to untreated (control) counterparts (FIG. 6, panel a). As anticipated, this was found to be directly associated with higher expression of tight junction proteins including zonulin-1 (ZO1) and Occludin (Ocln) in the intestinal tissues of prebiotics-fed mice versus control group (FIG. 6, panel b). In addition, further gene expression analyses revealed lower expression of inflammatory markers including Interleukine-6 (IL-6), tumor necrosis factor-alpha (TNF-α) and chemokine (C—C motif) ligand 2 (Ccl2) and monocyte chemoattractant protein 1 (MCP1) in the intestine of all of the prebiotics-fed mice groups as compared to control. IL-6 was significantly low in acorns-fed mice; TNF-α was significantly low in sago group; while MCP1 was significantly low in all of the three prebiotics groups (FIG. 6, panel c). Overall, these results hint that prebiotics could help maintain lower/homeostatic gut permeability (gut 'leakiness') with lower intestinal mucosal inflammation.

Prebiotics increase hypothalamic energy sensing to regulate/prevent the hallmarks of obesity. In an attempt to further estimate whether (and how) prebiotics could interact with gut-brain axis in the hypothalamus region of brain that regulates energy balance via modulating Agouti-related peptide (AgRP), neuropeptide Y (NPY) and Pro-opiomelanocortin (POMC), we found that mice fed with prebiotics— especially acorns—demonstrated significantly higher mRNA expression of POMC and insignificantly (slightly)

lower expression of AgRP and NPY (FIG. 6, panel d). These results hinted that these prebiotics modulated the expression of hypothalamic energy regulating neuronal proteins thereby leading to better energy sensing capacity and whole body energy metabolism regulation.

DISCUSSION

Prevalence of obesity and type 2 diabetes (T2D) is constantly increasing worldwide, raising an urgent need to develop preventive/therapeutic strategies that can halt this rate. Involvement of gut microbiome in obesity/T2D pathology has become evident from recent reports [32, 33]; hence, the use of gut microbiome modulators such as prebiotics are seen as vital approaches to prevent/ameliorate obesity/T2D epidemic [34, 35]. In addition, the demand of prebiotics is ever-increasing, owing to a plethora of other health-promoting effects [36], again underpinning the need to develop novel health-beneficial prebiotics from natural resources. In this milieu, we herein aimed to isolate and extract some novel prebiotic substrates from unique raw materials and finally selected acorns- and sago-derived prebiotics to examine their influence on human (ex-vivo) and mouse (in-vivo) gut microbiome and SCFAs proportions as well as their impact on the metabolic health of obesity and T2D in mice. We also compared throughout our study the efficacy of these selected prebiotics with the most-widely studied prebiotics i.e., inulin, and interestingly found that our new prebiotics are at least equivalent—or maybe even superior in several effects—to inulin, particularly in terms of several biological outcomes including microbiome-mediated SCFAs production and prevention of features of HFD-induced obesity and T2D via modulation of gut-brain axis.

Typically, prebiotics consist of dietary fibers and oligosaccharides. On the basis of high fiber content, we initially selected five raw materials including acorn, quinoa, sago, and sunflower and pumpkin seeds as potential sources of novel prebiotics. Acorn and sago demonstrated the highest yield of polysaccharides with least protein contamination along with superior amylase resistance, thus exhibiting appropriate prebiotics properties. Interestingly, we found that these selected prebiotics were fermentable by human gut microbiome to produce SCFAs in the fecal microbiome culture system in a way similar to that seen for inulin. Most importantly, we for the first time endeavored to prognosticate the influence of prebiotics on the spectrum of fecal microbiome and its secondary metabolites i.e., SCFAs in healthy versus diseased subjects by exploiting an ex-vivo incubation system established and validated previously by us [28] and other researchers [37]. The results from this trial convincingly show that each of these prebiotics modulated the gut microbiome and SCFAs levels differently in healthy versus diseased fecal cultures, thus suggesting that the health status of the host may influence the effects of prebiotics on gut microbiome and intestinal organic environment. Apparently, diseased conditions generally present with gut microbiome dysbiosis with reduced population of beneficial microbial groups and hence might extend more opportunities for prebiotics to promote the levels of such beneficial microbes and their metabolites that could benefit to combat the disease. Given that the composition of gut microbiome in healthy subjects versus patients with different diseases is generally found to be different, supplementation of prebiotics can be envisaged to favor the growth of specific bacterial groups in these patients that may further cross-feed other/ partner bacteria while suppressing several other bacterial groups via competition for nutrients and adherence sites and/or by producing inhibitory compounds.

Our results prominently showed that the inoculation of acorn- and sago-prebiotics significantly changed the human fecal microbiome signature, as evident from higher microbial diversity in terms of α-diversity indices including Shannon index, Chao1 and observed OTUs in all of the three prebiotics intervention groups, suggesting that selected prebiotics improved the fecal microbiome composition. Interestingly, albeit not surprisingly, PCoA analyses manifested that all three prebiotics induced more prominent changes in the feces of diseased subjects than of healthy volunteers, suggesting that the beneficial attributes of prebiotics could be more effective in modulating the configuration of gut microbiome in diseased subjects than in healthy microbiome milieus, plausibly because the microbiome in a healthy gut is already diverse, healthy or homeostatic enough. Prebiotics inoculation also appeared to increase the metabolic activity of the human fecal microbiome as evident from higher SCFAs levels and lower fecal pH. Intestinal pH slightly lower than neutral is generally associated with beneficial effects such as constrained growth of various opportunistic pathogens or indigenous pathobionts [38, 39]. For instance, several fruits and resistance starch are known to exhibit beneficial effects via maintaining slightly acidic gut organic environment. Furthermore, we noted that the prebiotics-inoculated fecal specimens had higher levels of SCFAs viz. acetate, propionate and lactate; however, these patterns also differed between specimen from healthy versus diseased subjects. For example, acetate was higher in the feces of healthy donors but lower in diseased counterpart upon prebiotics interventions. All the prebiotics-treated samples had higher propionate in both healthy and diseased fecal cultures, with no significant differences in butyrate levels, suggesting that selected prebiotics including inulin treatments preferentially increased propionate production capacity of the human fecal microbiome. Propionate is known to possess several health benefits including improved serum cholesterol levels and lower lipogenesis and incidences of carcinogenesis in different tissues [40, 41]. Interestingly, propionate levels were higher in inulin- and acorn-inoculated healthy feces but only in acorn-enriched diseased feces. More strikingly, in healthy feces, higher propionate levels were positively correlated with the abundance of *Bacteroidetes, Prevotella, Faecalibacterium* and *Succinivibrio* in acorns-inoculated samples and with higher *Lactobacillus* abundance in inulin-treated feces. Whereas, in diseased feces, *Sutterella* was the major bacterial genus correlated with higher propionate concentration. These results indicate that the role of different microbial species in producing propionate or the population of propionate-producers per se might differ according to the fecal microbiome in healthy versus diseased subjects. Although, these exciting results established that selected prebiotics are fermentable by human-gut microbiome and produce beneficial SCFAs using ex-vivo human fecal culture system, however, such effects might be different when directly fed to humans, hence further clinical studies are warranted to determine the such effects.

In addition to ex-vivo effects on human fecal microbiome, we also investigated the beneficial impact of selected prebiotics on HFD-induced obesity and T2D in mice, emphasizing mainly on a plausible mechanism i.e., the modulation of gut-brain axis. Prebiotics appeared to prevent HFD-induced glucose intolerance and insulin resistance without affecting body weight and adiposity. Interestingly, such improvements were superior specifically in acorn- than inulin-fed mice. Based on these results, prebiotics appeared to have preserved a better metabolic function to maintain normal glucose homeostasis. This might be through better maintenance of insulin sensitivity (as indicated by better ITT function) in peripheral metabolic organs like adipose tissues and liver [42]. This can be supported by evidences that prebiotics feeding decreases fat accumulation in adipocytes and hepatocytes, since intracellular fat accumulation is detrimental for insulin sensitivity and instigates insulin resistance (a hallmark of T2D) [43]. Low-grade inflammation is another crucial factor that impacts insulin actions; however, the source of this inflammation is not precisely known. It is hypothesized that the gut microbiome may be the primary source of inflammatory signals such as lipopolysaccharide (LPS) and cause endotoxemia due to increased gut permeability (leaky gut). We noted a dramatically lower gut permeability in prebiotics-fed versus control (HFD-fed) mice, which may be attributed to higher expression of tight-junction proteins including ZO-1 and Occludin.

Furthermore, we also noted lower expression of inflammatory genes including IL-6, TNF-α and MCP-1 in the intestinal tissues of prebiotics-fed mice, suggesting that enteric mucosal inflammation remain significantly decreased/controlled upon prebiotics feeding. Interestingly, SCFAs, especially butyrate and propionate (which were higher in prebiotics-fed mice) are known to reduce gut permeability [44, 45]. Anti-inflammatory actions of SCFAs, mainly via reducing TNF-α production and attenuation of NF-κB activation, have also been reported [46]. Indeed, this decreased gut leakiness along with reduced inflammation may contribute to maintain normal glucose homeostasis even in metabolically stressed conditions such as HFD-feeding.

Gut-brain axis, particularly the hypothalamic signals, are also known to play an important role in the regulation of whole body metabolism [47-49]. We also found slightly increased POMC and decreased AgRP and NPY in the hypothalamus of prebiotics-fed mice, suggesting that the effects of prebiotics in the gut could be signaled into the hypothalamus (a metabolic regulating center). Increased POMC (anorexigenic) and decreased AgRP and NPY (orexigenic) can be involved in food intake behavior; however, we did not see any notable difference in food intake upon prebiotics feeding. Hence, the beneficial effects of these prebiotics on glucose homeostasis could be explained in two possible ways: 1) changes in POMC, AgRP and NPY are too marginal to affect intake behaviors but may impact whole body metabolic rate, as increased POMC enhances whole body metabolic rate; and 2) gut microbiome modulation with increased propionate and decreased gut permeability and inflammation may favor enhanced insulin sensitivity to control glucose homeostasis. Nevertheless, our data concur with other studies reporting that feeding of prebiotics (resistance starch) reduces POMC expression in hypothalamus with no significant changes in AgRP and NPY [50], suggesting that some prebiotic effects might be associated exclusively or more closely with POMC. However, whether and how prebiotic feeding and consequent increased propionate may increase hypothalamic expression of POMC remains unclear and should be an interesting subject for future studies.

Mouse and human gut microbiota are different in terms of both composition as well as function of bacterial strains; however, we noted several effects of these three prebiotics that were common in both mouse and human feces, indicating that (a) the effects of these prebiotics are consistent with regard to specific bacteria independent of the host species and (b) the ex-vivo human fecal slurry system used in here can be exploited as a useful model to predict the effects of such dietary ingredients on fecal microbiota. For example, the relative abundance of the family Enterobacteriacea (and phylum Proteobacteria) was decreased by each of the three prebiotics in all of the three models i.e., healthy and diseased human feces as well as in the mouse gut. This effect might also corroborate the beneficial effects of these prebiotics because Enterobacteriaceae includes, besides several benign gut symbionts, many opportunistic gut pathobionts such as *E. coli, Enterobacter, Salmonella, Yersinia, Klebsiella, Shigella, Proteus* and *Citrobacter*. Likewise, the abundance of the genus *Erwinia* (another opportunistic pathogen belonging to the family Enterobacteriaceae) was decreased by all three prebiotics in both healthy and diseased human feces but not in mouse possibly because its carriage in mouse gut is already too low to be detected. The fecal pH was also decreased by all three prebiotics in all of the three fecal specimens, suggesting increased metabolic activities of fecal bacteria that may have checked the population of these subdominant pathobionts. The abundance of *Bacteroides* was increased by both Acorn and Sago prebiotics (but not by inulin) in both mouse and human feces. This effect might be ascribed to differences in the biochemistry of these three polysaccharides. Inulin is a polymer composed mainly of fructose units (fructo-oligasaccharide) [51, 52], while acorn [53] and sago polysaccharides can include amylose and amylopectin and hence can be considered as a kind of resistant starch. Therefore, it is likely that these compounds would favor the growth of *Bacteroides*, which are efficient degraders of intact and insoluble plant cell walls and similar complex dietary fibers. This biochemical difference may also underlie the increased abundance of lactic acid bacteria including *Lactobacillus, Bifidobacterium* and *Enterococcus* by inulin—but not acorn and sago polysaccharides—in mouse and human feces. Nevertheless, we also observed several effects that were specific to type of host or the prebiotic. For example, the abundance of the phylum *Firmicutes*, the families Peptococcaceae and Erysipelotrichaceae, and the genera *Oscillospira, Desulfovibrio, Bilophila* and *Muscispirillum* was lowered by all three prebiotics only in mice but not in human specimens. *Faecalibacterium*, which is a beneficial gut bacterium [54-56], was increased by all three prebiotics only in the feces of diseased human subjects but not in healthy humans or in mice. The abundance of the genera *Lactococcus* and *Parabacteroides* increased in both humans and mice but only by Sago. Butyrate was increased by all three prebiotics in mice but not in human feces, while lactate and propionate levels were increased variably by acorn and sago in both human and mouse feces (data not shown). The data suggest that while many effects of these 3 prebiotics are consistence, some effects are prebiotics and host specific, however further studies are needed to establish such facts.

We clearly demonstrate the beneficial effects of prebiotics in the prevention of HFD-induced obesity and T2D, and future studies will confirm the therapeutic, in addition to preventative, importance of prebiotics against diet-induced obesity and T2D. Prebiotics seem to mediate lower gut permeability by enhancing tight junctions and suppressing inflammatory signals along with increased energy sensing molecules (POMC) via modulating gut microbiome-SCFAs interface, thus leading us to propose a physiological mechanism of gut-microbiome-brain axis to prevent obesity and T2D; however, the involvement of specific cell types and underlying mechanism(s) remain to be illustrated. Future studies focusing on how prebiotics mediate gut microbiome metabolites like SCFAs via interactions with signaling molecules (e.g., FFAR2/3) will be of high significance to decipher the molecular mechanism(s).

The present study was executed using a translational approach to test the effects of selected prebiotics in human fecal culture system ex-vivo, thereby making a strong foundation for determining (prognosticating) the interaction of prebiotics with human gut microbiome. No doubt, such a culture system may have its own limitations and may not truly mimic the physiological effects happening in human gut in-vivo and hence future more-inclusive molecular and clinical studies remain indispensable to validate and explicate these benefits. We only demonstrate partial chemical characterization of newly isolated prebiotics and hence further analysis of chemical characteristics (e.g., glycomics approaches) are requisite. Nevertheless, these limitations also provide avenues for future studies that will not only fill the gaps in current knowledge but will also provide avenues confirming potential industrial and clinical applications of thesel prebiotics.

In conclusion, we herein demonstrate a new set of prebiotics from novel sources that could be exploited to ameliorate obesity and type 2 diabetes via modulating gut-microbiome-brain axis.

Materials and Methods

Extraction and preparation of polysaccharides from acorn, quinoa, and sunflower and pumpkin seeds: Sunflower seeds, pumpkin seeds and quinoa were purchased from Food to Live®, NY, USA. Acorns were purchased from local market of Baghmalek, Iran. After careful cleaning and inspection, the seeds were grounded in a home miller (RRH-A500, China) and passed through a 80-mesh screen. Defatting of powders was done using three volumes of ethanol at 60° C. for 12 h; for sunflower and pumpkin seeds, two extra defatting procedures were done with hexane for 12 h before ethanol defatting. Defatted and air dried powders were suspended in distilled water (1:10 w/v) and subsequently, hot water extraction of polysaccharides was done at 90° C. for 3 h in water bath (Precision®, USA). Following centrifugation of extracts (2000×g for 10 min, at 20° C.), the insoluble residues were removed and the supernatant was then precipitated by adding ethanol (48 h, 4° C.) to a final concentration of 80% (v/v). After collecting by centrifugation (8000×g, 10 min, at 4° C.), the precipitate polysaccharides were washed three times with ethanol. For sunflower and pumpkin seed which had high protein contamination, deproteinization was done by the TCA method for three times, as following: pH of crude was adjusted to 3.0 with TCA solution (10%) and kept overnight. After centrifugation for 10 min at 5,000 rpm, the deproteinized supernatant was kept for ethanol participation. Finally, the precipitate was dissolved in deionized water and dried in a freeze-dryer (LABCONE, Freezone 4.5, USA). The yield of obtained polysaccharides was calculated as the weight of obtained powders divided by the initial weight of seeds.

Preparation of resistant starch from sago starch: Sago (Sabudana) starch was purchased from Jalipur Millers, UK. Preparation of Resistant starch from sago starch was done according to the modified method of Purwani et al. [51], and Siew-Wai et al. [57]. Sago starch was suspended in starch in water (1:20 w/v) and boiled and stirred on plate heater for 10 minutes. After autoclaving at 121° C. (1.2 atm) for 1 h, the gel was kept at 4° C. overnight to develop retro-gradation. Enzymatic hydrolysis of retrograded starch suspension was done by adding 2 units/mL of α-amylase (Sigma-Aldrich, USA) and 1 mL of Pullulanase microbial (Sigma-Aldrich, USA) and incubating for 24 h at 70° C. in a shaker incubator (150 rpm). This process was repeated twice. Hydrolyzed starch was centrifuged for 10 min at room temperature and the obtained pellets were freeze-dried in a freeze-dryer (LABCONE, Freezone 4.5, USA).

Resistance to acidic and enzymatic digestion: Resistance of acorn polysaccharide powder samples to acidic and enzymatic digestion was determined and compared based n the method of Tadayoni et al. [58]. Simulated gastric fluid (SGF; pH 1.2) consisted of NaCl (2 g) and HCl (7 ml) while simulated intestinal fluid (SIF; pH 7.4) included $KH_2PO_4$ (6.8 g), NaOH (190 ml) and α-amylase (2 unit/ml) (Sigma-Aldrich). Reproduction of a mixture of simulated gastric and intestinal fluid (SMF; pH 4.5) was achieved by mixing SGF and SIF at a ratio of 39:61. Dissolution was carried out in 900 ml of dissolution medium, which was stirred at 100 rpm at 37° C. A sample was taken at 1, 2, 3 h to determine the percentage of hydrolysis, which was calculated based on the reduction of liberated sugar and total sugar content according to 3,5-Dinitrosalicylic acid (DNS) and phenol-sulfuric acid method.

Chemical characterization of polysaccharides: The total sugar content of the polysaccharides, as an indicator of purity, was measured by phenol sulphuric acid method. Protein quantification was based on the bicinchoninic acid (BCA) method using bovine serum albumin (BSA) as standard, using the Pierce™ BCA Protein Assay Kit (Thermo scientific, USA). Total phenolic composition was determined by the Folin-Ciocalteu colorimetric method, using gallic acid for making the standard curve. The presence of free carbonyl group (C=O), reducing sugars, was determined by DNS method using glucose as a standard. The antioxidant activity of methanol extraction of polysaccharides powders, based on the scavenging activity of the 1,1-diphenyl-2-picrylhydrazyl (DPPH) free radical, was determined by the method described by Que et al. [59].

Human fecal microbiome fermentation model: The culture media used for doing ex-vivo human fecal slurry fermentation experiment was prepared according to the recipe devised by Vester-Boler et al. [37]. Fresh fecal samples were collected from two healthy volunteers and two heart disease patient donors and were immediately stored at −80° C. until further use. For the preparation of fecal slurry, the samples were thawed and diluted (1:10 W/V) in anaerobic dilution solution (NaCl 5; glucose 2; Cysteine-HCl 0.3; g/L) and vortexed for 15 minutes or until completely homogenized. The fecal specimens of two healthy and two diseased subjects were pooled, respectively, before the dilution step in order to obtain the two final aliquots, one each of healthy and diseased fecal specimen. The homogenized mixture was filtered through four layers of cheesecloth and was immediately used for inoculation in tubes containing media (control groups) or a combination of media plus fibers (treatment groups). All of the steps involved in inoculum preparation were done inside the anaerobic chamber (Forma anaerobic system, Thermo Scientific, USA). In-vitro anaerobic fermentation using homogenized fecal specimens of healthy and diseased subjects were grouped as follows: a) Control: fermentation media without fiber, b) Control+1% Inulin, c) Control+1% Acorn Polysaccharide, and d) Control+1% Sago resistance starch. Three hundred mg of each fiber was added in a 50 ml tube followed by the addition of 26 mL fermentation media to each tube; in triplicates. These tubes were kept inside the anaerobic chamber for 24 h to allow hydration of samples before starting the fermentation experiment. At the beginning of the experiment, 4 mL of freshly prepared fecal inoculums was added in each tube and the tubes were incubated at 37° C. for 24 h in the anaerobic chamber with periodic mixing. At 0, 3, 6, 9 and 24 h during fermentation, samples were taken out. An aliquot was used for pH measurement using a laboratory pH meter; the remaining sample was centrifuged at 14000 g, 10 minutes at 4° C. and the supernatant was immediately frozen for SCFAs analysis and the pellet was stored at −80° C. for microbiome analysis. The whole anaerobic fermentation experiment was performed twice with triplicates each time and hence the data presented here are the mean of a total of six replicates. However, for cost effectiveness, replicates from each experiment was pooled (i.e., $1^{st}$ replicate of first experiment was pooled with $1^{st}$ replicate of second experiment), and resulted pooled replicates were separately analyzed for microbiome sequencing. The microbiome composition analysis was done on 0 hrs (before prebiotics inoculation) and after 9 hrs prebiotics inoculation samples only, as our earlier studies shows that gut microbiome signature after 9 hrs in fecal slurry conditions too enriched with Proteobacteria, and start losing diversity in control samples [28], hence the data presented here is only after 9 hrs of prebiotics inoculation.

Gut microbiome analysis: 16S rRNA gene amplification and sequencing was executed as per our method described elsewhere [28, 60, 61]. Briefly, approximately 200 mg of fecal slurry pellets or mice feces was used to extract genomic DNA using Qiagen DNA Stool Mini Kit (Qiagen, CA, USA) according to the manufacturer instructions, with a slight modification i.e., using lysis temperature of 95° C. instead of 75° C. for efficient lysis and DNA yield of gram-positive bacteria. The hypervariable region V4 of bacterial 16S rRNA gene was amplified using the primers 515F (barcoded) and 806R in accordance with the Earth Microbiome Project protocol, with the minor modification as described previously [62]. The resulting amplicons were purified by using AMPure® magnetic purification beads (Agencourt) and the purified PCR products were quantified by using Qubit-3 fluorimeter (InVitrogen). Equal amounts of purified products were pooled; and the pool was quantified again, normalized to 4 nm, denatured and diluted to 8 pM and was sequenced on an Illumina MiSeq sequencer (using Miseq reagent kit v3). The sequences were de-multiplexed, quality filtered, clustered and analyzed using the Quantitative Insights into Microbial Ecology (QIIME, version 1.9.1) software. To avoid bias due to different sequencing depth, the OTU tables were rarefied to the lowest number of sequences per sample (human fecal slurry specimens: 15,358 sequences per sample; mice samples: 20,000 sequences per sample) for computing alpha-diversity metrics within QIIME. Linear discriminant analysis (LDA) analysis and Cladograms were developed on genus level data using LDA effect size (LefSe)[63] on Galaxy platform (huttenhower.sph.harvard.edu/galaxy/). OTUs with abundances higher than 1% were included in the subsequent analyses. Taxonomy assignment and diversity analyses were computed within QIIME to compare bacterial species richness between the different experimental groups. Alpha-diversity (rarefaction curve for observed OTUs, Chao1, PD Whole Tree and Shannon) indices were computed with core_diversity_analysis.py script. Beta-diversity was generated within QIIME by using weighted and unweighted Unifrac distance matrices. Principal components analysis (PCoA) was performed (using EMPeror version 0.9.3-dev) to determine the influence of different prebiotics treatments on the overall microbiome composition. The data of bacterial diversity and abundance between the different groups within the same study were compared using non-parametric tests in R statistical software package (version 3.4.3; www.r-project.org/). Statistically significant differences in the abundance of microbial groups between different prebiotics groups were calculated by Kruskal-Wallis test followed by Dunn's post-hoc analysis.

Short-chain fatty acid analysis: During the fermentation, samples were taken every 3 hours, and supernatants were collected after centrifugation (12,000 g, 10 min). Concentrations of SCFAs (lactate, acetate, propionate and butyrate) were determined using a high-performance liquid chromatography (Waters-2695 Alliance HPLC system, Waters Corporation, Milford, MA, USA) with DAD detector at 210 nm, equipped with a Aminex HPX-87H column (Bio-Rad Laboratories, Hercules, CA). $H_2SO_4$ (0.005 N) was used to elute the column with a flow rate of 0.6 ml/min at 25° C.

Mouse HFD-Feeding Experiment:

Mice: C57BL/6J mice (n=8-9 in each group; age 8-10 weeks) were randomized into 4 groups; 1) HFD-control; fed with 60% HFD (Research Diets Inc.), 2) HFD-Inulin: fed with HFD supplemented with 5% inulin (Sigma-Aldrich) HFD-Acorn-PS: fed with HFD supplemented with 5% acorn polysaccharides (PS), and 4) HFD-Sago-PS: fed with HFD supplemented sago PS. Food and water were fed ad-libitum for 8 weeks to induce obesity and insulin resistance, and diet intake was measured daily. Body weight was measured and fresh fecal samples were collected once every week. All animal studies and protocols were approved by the Wake Forest Animal Research Program's Institutional Animal Care and Use Committee.

Glucose and insulin tolerance tests: Oral and intra-peritoneal (i.p.) glucose tolerance test was performed by glucose (2 mg/g body weight) by oral gavage and intraperitoneal injection, respectively, to overnight fasted mice. For insulin tolerance test, 4-6 hrs fasted mice were given i.p. 0.75 U/kg body weight of insulin (Humulin). Blood glucose was measured at 0 min (before administration of glucose or insulin), 15, 30, 60 and 120 min after glucose/insulin administration using AccuCheck glucometer kit.

Gut physiology measurements: The impact of prebiotics on gut physiological measures i.e., fecal frequency per hour, fecal weight dropped per hour, fecal water content and fecal pH was assessed after 8 weeks of starting prebiotics feeding.

In-vivo gut permeability assay: Four hours after orally administering 4 kDa FITC-dextran (60 mg/100 gm body weight) to 4 h-fasted mice, the fluorescence intensity in blood collected from the tail vein was measured to determine the gut permeability (intestinal 'leakiness')[64, 65].

Organ weight measurements: After euthanizing mice, fat depots from different sites of body i.e., white adipose tissue (WAT) from mesenteric WAT (mWAT), gonadal WAT (gWAT). retroperitoneal WAT (rWAT), anterior subcutaneous WAT (aWAT) and posterior subcutaneous WAT (pWAT), brown adipose tissue (BAT), and other organs like caecum, liver and skeletal muscles (Quadriceps), were collected and weighted.

Histological analyses: Mouse gWAT, BAT, ileum and colon were fixed in 10% neutral buffered formalin, processed into paraffin blocks, sectioned at 6 microns, and stained with hematoxylin and eosin. Stained sections were examined by light microscopy (AmScope) and pictures were captured using 9MP digital camera (MU900, AmScope) and images were analyzed using ImageJ software.

Real-time PCR: Snap-frozen intestine (ileum) and hypothalamus were used for isolating total RNA using RNeasy kit (Qiagen, Gaithersburg, MD), that was reverse transcribed to complementary cDNA using ABI reverse transcription kit. Quantitative gene expression of tight-junction genes including zonulin-1 (ZO-1) and Occludin (Ocln), inflammatory markers including interleukine-6 (IL-6), tumor necrosis factor-alpha (TNF-a) and chemokine (C—C motif) ligand 2/monocyte chemoattractant protein 1 (Ccl2/MCP1), and hypothalamic energy sensing genes including Agouti related protein (AgRP), neuropeptide Y (NPY) and Pro-opiomelanocortin (POMC) was measured by real-time PCR (ABI 7500; Applied Biosystems). The expression of 18S gene served as an internal control. Three to four independent samples were prepared from 4-6 different mice per treatment group and PCR reactions were carried out in triplicate. The results were expressed as fold difference in gene expression relative to expression in control group normalized with 18S expression, as described in our previous report [66-68].

Statistical analysis: For mouse studies, data are expressed as mean±SEM. Statistical significance between groups was determined using unpaired two-tailed Student's t-test or one-way analysis of variance. $P < 0.05$ was considered statistically significant and all tests were two-sided.

REFERENCES

[1] Marti J M, Martinez-Martinez D, Rubio T, Gracia C, Pena M, Latorre A, et al. Health and Disease Imprinted in the Time Variability of the Human Microbiome. mSystems. 2017; 2.

[2] Lynch S V, Pedersen O. The Human Intestinal Microbiome in Health and Disease. N Engl J Med. 2016; 375:2369-79.

[3] Cho I, Blaser M J. The human microbiome: at the interface of health and disease. Nat Rev Genet. 2012; 13:260-70.

[4] Integrative HMPRNC. The Integrative Human Microbiome Project: dynamic analysis of microbiome-host omics profiles during periods of human health and disease. Cell Host Microbe. 2014; 16:276-89.

[5] Kayshap P C, Quigley E M. Therapeutic implications of the gastrointestinal microbiome. Curr Opin Pharmacol. 2018; 38:90-6.

[6] Dahiya D K, Renuka, Puniya M, Shandilya U K, Dhewa T, Kumar N, et al. Gut Microbiota Modulation and Its Relationship with Obesity Using Prebiotic Fibers and Probiotics: A Review. Front Microbiol. 2017; 8:563.

[7] Yadav H, Jain, S., Bissi, L., Marotta, F. Gut Microbiome Derived Metabolites to Regulate Energy Homeostasis: How Microbiome Talks to Host. Metabolomics. 2016; 6:e150.

[8] Ferrario C, Statello R, Carnevali L, Mancabelli L, Milani C, Mangifesta M, et al. How to Feed the Mammalian Gut Microbiota: Bacterial and Metabolic Modulation by Dietary Fibers. Front Microbiol. 2017; 8:1749.

[9] Wilson B, Whelan K. Prebiotic inulin-type fructans and galacto-oligosaccharides: definition, specificity, function, and application in gastrointestinal disorders. J Gastroenterol Hepatol. 2017; 32 Suppl 1:64-8.

[10] de Vrese M, Schrezenmeir J. Probiotics, prebiotics, and synbiotics. Adv Biochem Eng Biotechnol. 2008; 111:1-66.

[11] Slavin J. Fiber and prebiotics: mechanisms and health benefits. Nutrients. 2013; 5:1417-35.

[12] Balakrishnan M, Floch M H. Prebiotics, probiotics and digestive health. Curr Opin Clin Nutr Metab Care. 2012; 15:580-5.

[13] Louis P, Flint H J, Michel C. How to Manipulate the Microbiota: Prebiotics. Adv Exp Med Biol. 2016; 902: 119-42.

22

[14] Lin C S, Chang C J, Lu C C, Martel J, Ojcius D M, Ko Y F, et al. Impact of the gut microbiota, prebiotics, and probiotics on human health and disease. Biomed J. 2014; 37:259-68.

[15] Weitkunat K, Schumann S, Petzke K J, Blaut M, Loh G, Klaus S. Effects of dietary inulin on bacterial growth, short-chain fatty acid production and hepatic lipid metabolism in gnotobiotic mice. J Nutr Biochem. 2015; 26:929-37.

[16] Chen K, Chen H, Faas M M, de Haan B J, Li J, Xiao P, et al. Specific inulin-type fructan fibers protect against autoimmune diabetes by modulating gut immunity, barrier function, and microbiota homeostasis. Mol Nutr Food Res. 2017; 61.

[17] Kelly G. Inulin-type prebiotics: a review. (Part 2). Altern Med Rev. 2009; 14:36-55.

[18] Ahmadi S, Mainali, R., Nagpal, R., Sheikh-Zeinoddin, M., Soleimanian-Zad, S., Wang, S., Deep, G., Mishra, S. K., Yadav, H. Dietary Polysaccharides in the Amelioration of Gut Microbiome Dysbiosis and Metabolic Diseases. Obesity & Control Therapies. 2017; 4:1-15.

[19] Wang D, Sun F, Lu C, Chen P, Wang Z, Qiu Y, et al. Inulin based glutathione-responsive delivery system for colon cancer treatment. Int J Biol Macromol. 2018; 111: 1264-72.

[20] Qamar T R, Syed F, Nasir M, Rehman H, Zahid M N, Liu R H, et al. Novel Combination of Prebiotics Galacto-Oligosaccharides and Inulin-Inhibited Aberrant Crypt Foci Formation and Biomarkers of Colon Cancer in Wistar Rats. Nutrients. 2016; 8.

[21] Pool-Zobel B L. Inulin-type fructans and reduction in colon cancer risk: review of experimental and human data. Br J Nutr. 2005; 93 Suppl 1:S73-90.

[22] Bindels L B, Neyrinck A M, Salazar N, Taminiau B, Druart C, Muccioli G G, et al. Non Digestible Oligosaccharides Modulate the Gut Microbiota to Control the Development of Leukemia and Associated Cachexia in Mice. PLoS One. 2015; 10:e0131009.

[23] Everard A, Lazarevic V, Derrien M, Girard M, Muccioli G G, Neyrinck A M, et al. Responses of gut microbiota and glucose and lipid metabolism to prebiotics in genetic obese and diet-induced leptin-resistant mice. Diabetes. 2011; 60:2775-86.

[24] Costabile A, Deaville E R, Morales A M, Gibson G R. Prebiotic Potential of a Maize-Based Soluble Fibre and Impact of Dose on the Human Gut Microbiota. PLoS One. 2016; 11:e0144457.

[25] Long W, Xue Z, Zhang Q, Feng Z, Bridgewater L, Wang L, et al. Differential responses of gut microbiota to the same prebiotic formula in oligotrophic and eutrophic batch fermentation systems. Sci Rep. 2015; 5:13469.

[26] Vigsnaes L K, Holck J, Meyer A S, Licht T R. In vitro fermentation of sugar beet arabino-oligosaccharides by fecal microbiota obtained from patients with ulcerative colitis to selectively stimulate the growth of *Bifidobacterium* spp. and *Lactobacillus* spp. Appl Environ Microbiol. 2011; 77:8336-44.

[27] Takagi R, Sasaki K, Sasaki D, Fukuda I, Tanaka K, Yoshida K, et al. A Single-Batch Fermentation System to Simulate Human Colonic Microbiota for High-Throughput Evaluation of Prebiotics. PLoS One. 2016; 11:e0160533.

[28] Nagpal R, Wang S, Ahmadi S, Hayes J, Gagliano J, Subashchandrabose S, et al. Human-origin probiotic cocktail increases short-chain fatty acid production via modulation of mice and human gut microbiome. Sci Rep. 2018; 8:12649.

[29] Jain S K, Jain A, Gupta Y, Ahirwar M. Design and development of hydrogel beads for targeted drug delivery to the colon. AAPS PharmSciTech. 2007; 8:E56.

[30] Holscher H D. Dietary fiber and prebiotics and the gastrointestinal microbiota. Gut Microbes. 2017; 8:172-84.

[31] Viladomiu M, Hontecillas R, Yuan L, Lu P, Bassaganya-Riera J. Nutritional protective mechanisms against gut inflammation. J Nutr Biochem. 2013; 24:929-39.

[32] Barlow G M, Yu A, Mathur R. Role of the Gut Microbiome in Obesity and Diabetes Mellitus. Nutr Clin Pract. 2015; 30:787-97.

[33] Wu H, Esteve E, Tremaroli V, Khan M T, Caesar R, Manneras-Holm L, et al. Metformin alters the gut microbiome of individuals with treatment-naive type 2 diabetes, contributing to the therapeutic effects of the drug. Nat Med. 2017; 23:850-8.

[34] Tilg H, Gasbarrini A. Prebiotics for obesity: a small light on the horizon? Gut. 2013; 62:1096-7.

[35] Nicolucci A C, Hume M P, Martinez I, Mayengbam S, Walter J, Reimer R A. Prebiotics Reduce Body Fat and Alter Intestinal Microbiota in Children Who Are Overweight or With Obesity. Gastroenterology. 2017; 153:711-22.

[36] Patel S, Goyal, A. The current trends and future perspectives of prebiotics research: a review. 3 Biotech. 2012; 2:115-25.

[37] Vester Boler B M, Rossoni Serao M C, Faber T A, Bauer L L, Chow J, Murphy M R, et al. In vitro fermentation characteristics of select nondigestible oligosaccharides by infant fecal inocula. J Agric Food Chem. 2013; 61:2109-19.

[38] Percy-Robb I W, Collee J G. Bile acids: a pH dependent antibacterial system in the gut? Br Med J. 1972; 3:813-5.

[39] Kamada N, Chen G Y, Inohara N, Nunez G. Control of pathogens and pathobionts by the gut microbiota. Nat Immunol. 2013; 14:685-90.

[40] Hosseini E, Grootaert C, Verstraete W, Van de Wiele T. Propionate as a health-promoting microbial metabolite in the human gut. Nutr Rev. 2011; 69:245-58.

[41] Reichardt N, Duncan S H, Young P, Belenguer A, McWilliam Leitch C, Scott K P, et al. Phylogenetic distribution of three pathways for propionate production within the human gut microbiota. ISME J. 2014; 8:1323-35.

[42] Rosen E D, Spiegelman B M. Adipocytes as regulators of energy balance and glucose homeostasis. Nature. 2006; 444:847-53.

[43] Taylor R. Insulin resistance and type 2 diabetes. Diabetes. 2012; 61:778-9.

[44] Tedelind S, Westberg F, Kjerrulf M, Vidal A. Anti-inflammatory properties of the short-chain fatty acids acetate and propionate: a study with relevance to inflammatory bowel disease. World J Gastroenterol. 2007; 13:2826-32.

[45] Ohata A, Usami M, Miyoshi M. Short-chain fatty acids alter tight junction permeability in intestinal monolayer cells via lipoxygenase activation. Nutrition. 2005; 21:838-47.

[46] Vinolo M A, Rodrigues H G, Nachbar R T, Curi R. Regulation of inflammation by short chain fatty acids. Nutrients. 2011; 3:858-76.

[47] van de Wouw M, Schellekens H, Dinan T G, Cryan J F. Microbiota-Gut-Brain Axis: Modulator of Host Metabolism and Appetite. J Nutr. 2017; 147:727-45.

[48] Stanley S A, Kelly L, Latcha K N, Schmidt S F, Yu X, Nectow A R, et al. Bidirectional electromagnetic control of the hypothalamus regulates feeding and metabolism. Nature. 2016; 531:647-50.

[49] Coll A P, Yeo G S. The hypothalamus and metabolism: integrating signals to control energy and glucose homeostasis. Curr Opin Pharmacol. 2013; 13:970-6.

[50] Shen L, Keenan M J, Martin R J, Tulley R T, Raggio A M, McCutcheon K L, et al. Dietary resistant starch increases hypothalamic POMC expression in rats. Obesity (Silver Spring). 2009; 17:40-5.

[51] Purwani E Y, Purwadaria T, Suhartono M T. Fermentation RS3 derived from sago and rice starch with *Clostridium butyricum* BCC B2571 or *Eubacterium* rectale DSM 17629. Anaerobe. 2012; 18:55-61.

[52] Roberfroid M B. Caloric value of inulin and oligofructose. J Nutr. 1999; 129:1436S-7S.

[53] Ahmadi S, Sheikh-Zeinoddin M, Soleimanian-Zad S, Alihosseini F, Yadav H. Effects of different drying methods on the physicochemical properties and antioxidant activities of isolated acorn polysaccharides. Lwt. 2019; 100:1-9.

[54] Lopez-Siles M, Duncan S H, Garcia-Gil L J, Martinez-Medina M. *Faecalibacterium prausnitzii*: from microbiology to diagnostics and prognostics. ISME J. 2017; 11:841-52.

[55] Heinken A, Khan M T, Paglia G, Rodionov D A, Harmsen H J, Thiele I. Functional metabolic map of *Faecalibacterium prausnitzii*, a beneficial human gut microbe. J Bacteriol. 2014; 196:3289-302.

[56] Miguel S, Martin R, Rossi O, Bermudez-Humaran L G, Chatel J M, Sokol H, et al. *Faecalibacterium prausnitzii* and human intestinal health. Curr Opin Microbiol. 2013; 16:255-61.

[57] Siew-Wai L, Zi-Ni T, Karim A A, Hani N M, Rosma A. Fermentation of *Metroxylon* sagu resistant starch type III by *Lactobacillus* sp. and *Bifidobacterium bifidum*. J Agric Food Chem. 2010; 58:2274-8.

[58] Tadayoni M, Sheikh-Zeinoddin M, Soleimanian-Zad S. Isolation of bioactive polysaccharide from acorn and evaluation of its functional properties. Int J Biol Macromol. 2015; 72:179-84.

[59] Que F, Mao L, Zheng X. In vitro and in vivo antioxidant activities of daylily flowers and the involvement of phenolic compounds. Asia Pac J Clin Nutr. 2007; 16 Suppl 1:196-203.

[60] Nagpal R, Newman T M, Wang S, Jain S, Lovato J F, Yadav H. Obesity-Linked Gut Microbiome Dysbiosis Associated with Derangements in Gut Permeability and Intestinal Cellular Homeostasis Independent of Diet. J Diabetes Res. 2018; 2018:3462092.

[61] Nagpal R, Shively C A, Appt S A, Register T C, Michalson K T, Vitolins M Z, et al. Gut Microbiome Composition in Non-human Primates Consuming a Western or Mediterranean Diet. Front Nutr. 2018; 5:28.

[62] Nagpal R, Shively, C. A., Appt, S. A., Register, T. C., Michalson, K. T., Vitolins, M. Z., Yadav, H. Gut Microbiome Composition in Non-human Primates Consuming a Western or Mediterranean Diet. Frontiers in Nutrition. 2018.

[63] Segata N, Izard J, Waldron L, Gevers D, Miropolsky L, Garrett W S, et al. Metagenomic biomarker discovery and explanation. Genome Biol. 2011; 12:R60.

[64] Furuta G T, Turner J R, Taylor C T, Hershberg R M, Comerford K, Narravula S, et al. Hypoxia-inducible factor 1-dependent induction of intestinal trefoil factor protects barrier function during hypoxia. J Exp Med. 2001; 193:1027-34.

[65] Wang L, Llorente C, Hartmann P, Yang A M, Chen P, Schnabl B. Methods to determine intestinal permeability and bacterial translocation during liver disease. J Immunol Methods. 2015; 421:44-53.

[66] Yadav H, Quijano C, Kamaraju A K, Gavrilova O, Malek R, Chen W, et al. Protection from obesity and diabetes by blockade of TGF-beta/Smad3 signaling. Cell Metab. 2011; 14:67-79.

[67] Yadav H, Lee J H, Lloyd J, Walter P, Rane S G. Beneficial metabolic effects of a probiotic via butyrate-induced GLP-1 hormone secretion. J Biol Chem. 2013; 288:25088-97.

[68] Yadav H, Devalaraja S, Chung S T, Rane S G. TGF-beta1/Smad3 Pathway Targets PP2A-AMPK-FoxO1 Signaling to Regulate Hepatic Gluconeogenesis. J Biol Chem. 2017; 292:3420-32.

See also Ahmadi et al., "Prebiotics from acorn and sago prevent high-fat-diet-induced insulin resistance via microbiome-gut-brain axis modulation," J. Nutritional Biochem. 67 (2019) 1-13, which is incorporated by reference herein.

Example 2: Preparation of Bacteria and Milk to Produce Yogurt Food Product

Revive the frozen stocks: Five strains of probiotic *lactobacillus* strains—*L. rhamnosus* (D7.5), *L. paracasei* (D3.5), *L. plantarum* (D13.4), *L. plantarum* (D-6.1), and *L. rhamnosus* (D4.4)—were grown overnight in MRS media. Appropriate volume of bacterial suspension that gives $10^8$ CFU/mL in milk was then centrifuged and washed 2× with 0.85% NaCl.

TABLE 1

|  | D7.5 | D3.5 | D13.4 | D6.1 | D4.4 |
|---|---|---|---|---|---|
| Average Optical Density (OD) | 1.89 | 1.32 | 1.93 | 1.96 | 1.71 |
| CFU/mL | 3.067E+09 | 1.7E+08 | 2.77E+09 | 2.2E+09 | 4.5E+08 |

Preparation of yogurt starter: The pellet was then added and suspended in store-bought 2% reduced fat milk that was previously boiled in an autoclaved flask and allowed to cool to 37° C. The milk was incubated at 37° C. for 7-16 h then allowed to cool in 4° C. for 2 hrs to stop the fermentation process before further use.

$X$ (volume needed to add from fresh bacterial suspension)=$(10^8)$(final volume of milk)/(OD of bacterial suspension×$10^9$)

By following above protocol, we have determined the time of incubation for coagulating the milk for formation of yogurt and measured pH, syneresis and firmness (observational).

We have selected 14 hrs incubation time based on pH drop, syneresis profile and firmness. However, we found that yogurt prepared from these probiotics bacteria did not achieve a quality of optimal syneresis and firmness, while pH was optimal (pH ~4.5).

Preparation of Synbiotic Yogurt with 5% Sago and 0.175% Pectin:

To increase the firmness of our probiotic yogurt, we tested different concentrations of pectin (starting from 0.01, 0.05, 0.1, 0.125, 0.15, 0.175, 0.2, 0.225, and 0.25%), and found that 0.175% gives a good quality that is firm with less syneresis and with same pH (~4.5). To increase the biological activity, we added, 5% w/v freeze dried Sago according to our preclinical studies (as described in J Nutr Biochem paper) to achieve bioactive content of sago content in the synbiotic yogurt. Thus, the final synbiotic yogurt was developed by adding 5% freeze dried sago fibers and 0.175% pectin in 2% store bought milk and boiled. The milk was then allowed to cool to 37° C., and then the appropriate concentration of bacterial pellet ($10^8$ cfu/ml per strain) was resuspended in this milk. The milk was then incubated at 37° C. for 14 h and then allowed to cool in 4° C. for 2 hrs to stop the fermentation process before further use.

Preparation of Sago Fiber:

Water and sago (1:20 w/v) was boiled and stirred on hot plate for 10 min. After autoclaving at 121° C. (1.2 atm) for 1 h, the gel was kept at 4° C. overnight to develop retro-gradation. Enzymatic hydrolysis of retrograded starch suspension was done by adding 2 U/ml of α-amylase (Sigma-Aldrich, USA) and 1 ml of Pullulanase microbial (Sigma-Aldrich, USA) and incubating for 24 h at 70° C. in a shaker incubator (150 rpm). This process was repeated twice. Hydrolyzed starch was centrifuged for 10 min at room temperature, and the obtained pellets were freeze-dried in a freeze-dryer.

Example 3: Synbiotic Yogurt Ameliorates Type-2 Diabetes in Mice

We used the HFD-/streptozotocin (STZ)-induced mouse as a non-genetic model of T2D. T2D develops due to the combinatory effects of HFD and a single, low-dose intraperitoneal injection of STZ. STZ is specifically toxic to pancreatic β cells and leads to β-cell necrosis/partial cell death via its glucose transporter-mediated accumulation, DNA damage, and the production of reactive oxygen species and/or nitric oxide. We induced T2D through a single STZ injection (90 mg/kg body weight [BW]) after three weeks of HFD.

As shown in FIG. 7, there were no significant differences in fasting blood glucose (FBG) in any of the groups due to HFD alone (before STZ) (FIG. 7, panel a). After STZ, the FBG was significantly lower in the synbiotic yogurt-fed mice (P<0.001). Although there were no significant differences during Week 1 (P=0.125), weekly sub-analysis revealed that there were significant differences among the groups during Week 2, with the synbiotic yogurt-fed mice having the lowest average FBG (P<0.001). At baseline, there were no significant differences in meal tolerance between the groups (P=0.956) or the AUC (P=0.703). After five weeks of HFD, the synbiotic yogurt-fed mice demonstrated a lower rise in glucose during the meal tolerance test (MTT), but there was not a significant difference among the groups (P=0.052); however, the AUC revealed a significant difference (P=0.011) (FIG. 7, panels b, c). There were significant differences among the groups in daily body weight (BW) over the five-week study (P<0.001), with the control yogurt-fed mice having the lowest average (FIG. 7, panel d). The overall average change in daily BW was similar due to HFD alone (P=0.223), but was significantly different after STZ (P<0.001), with the control yogurt-fed mice exhibiting the largest decrease (FIG. 7, panel e). The average daily water intake was significantly different between the groups and the control-yogurt fed mice had the highest intake (P=0.019) (FIG. 7, panel f). The average food intake per day was similar between the groups (P=0.313) (data not shown).

The foregoing is illustrative of the present invention, and is not to be construed as limiting thereof. The invention is defined by the following claims, with equivalents of the claims to be included therein.

What is claimed is:

1. A method of improving leaky gut in a mammalian subject in need thereof, comprising administering to the subject an effective amount of a composition comprising polysaccharides isolated from sago or acorn, wherein said administering is by enteral administration.

2. The method of claim 1, wherein said administering is by oral administration.

3. The method of claim 1, wherein said subject is a human subject.

4. The method of claim 1, wherein said subject is a non-human mammalian subject.

5. The method of claim 1, wherein the composition is provided in a tablet or capsule.

6. The method of claim 1, wherein said polysaccharides are isolated from sago.

7. The method of claim 1, wherein said polysaccharides are isolated from acorn.

8. The method of claim 1, wherein said composition is provided in a nutritionally acceptable carrier.

9. The method of claim 8, wherein said nutritionally acceptable carrier comprises a food product.

10. The method of claim 9, wherein the food product is a dairy product.

11. The method of claim 9, wherein the food product comprises a probiotic.

12. The method of claim 9, wherein the food product is a yogurt comprising from 0.1 to 12% weight/volume of the polysaccharides isolated from sago.

13. The method of claim 12, wherein the yogurt further comprises:

pectin in an amount from 0.1 to 0.25% weight/volume; and probiotic *Lactobacillus* strain(s) in an amount from $10^7$ to $10^9$ CFU/mL of the yogurt.

14. A method of decreasing or controlling inflammation in the intestinal tissue of a mammalian subject in need thereof, comprising administering to the subject an effective amount of a composition comprising polysaccharides isolated from sago or acorn, wherein said administering is by enteral administration, and wherein expression of IL-6, TNF-$\alpha$, Ccl2 and/or MCP-1 genes is lowered.

15. The method of claim 14, wherein said composition is provided in a nutritionally acceptable carrier.

16. The method of claim 15, wherein said nutritionally acceptable carrier comprises a food product.

17. The method of claim 16, wherein the food product is a dairy product.

18. The method of claim 16, wherein the food product comprises a probiotic.

19. The method of claim 16, wherein the food product is a yogurt comprising from 0.1 to 12% weight/volume of the polysaccharides isolated from sago.

20. The method of claim 19, wherein the yogurt further comprises:

pectin in an amount from 0.1 to 0.25% weight/volume; and probiotic *Lactobacillus* strain(s) in an amount from $10^7$ to $10^9$ CFU/mL of the yogurt.

* * * * *